United States Patent [19]

Okamoto et al.

[11] 4,201,843

[45] May 6, 1980

[54] PROCESS FOR MANUFACTURING TYLOSIN DERIVATIVES

[75] Inventors: Rokuro Okamoto, Fujisawa; Tsumoru Fukumoto, Sagamihara; Akira Takamatsu, Yokohama; Tomio Takeuchi, Tokyo, all of Japan

[73] Assignee: Sanraku Ocean Co., Ltd., Tokyo, Japan

[21] Appl. No.: 881,279

[22] Filed: Feb. 27, 1978

Related U.S. Application Data

[62] Division of Ser. No. 708,151, Jul. 23, 1976, Pat. No. 4,092,473.

[30] Foreign Application Priority Data

Aug. 1, 1975 [JP] Japan .................................. 50/93053
Sep. 12, 1975 [JP] Japan .................................. 50/110010
Dec. 27, 1975 [JP] Japan .................................. 50/158388
May 15, 1976 [JP] Japan .................................. 51/55626

[51] Int. Cl.$^2$ .......................... C12P 19/62; C12R 1/55
[52] U.S. Cl. ......................................... 435/76; 435/898
[58] Field of Search ...................................... 195/80 R

[56] References Cited

U.S. PATENT DOCUMENTS 2,943,024  6/1960  Ninet et al. ......................... 195/80 R
3,817,836  6/1974  Theriault et al. .................... 195/80 R

OTHER PUBLICATIONS

The Merck Index, pp. 1260 and 1261, 9th Edition.

Primary Examiner—Alvin E. Tanenholtz
Attorney, Agent, or Firm—Frank J. Jordan

[57] ABSTRACT

New tylosin derivatives having at least one acyl group at the 3- and 4"-positions of tylosin, and the acid addition salts thereof, which inhibit the growth of various microorganisms including drug-resistant bacterial isolants and which produce high blood levels through oral administration are produced by a biochemical reaction using the microorganisms of the genus Streptomyces which are selected for their newly-found ability to acylate at least one of the 3- and 4"-positions of macrolide antibiotics; they are recovered from the reacted mixture by conventional methods for recovering macrolide antibiotics.

25 Claims, 24 Drawing Figures

PROCESS FOR MANUFACTURING TYLOSIN DERIVATIVES

This is a division of application Ser. No. 708,151, filed July 23, 1976 now U.S. Pat. No. 4,092,473.

BACKGROUND OF THE INVENTION (1) Field of the Invention

New tylosin derivatives having at least one acyl group at the 3- and 4"-positions of tylosin, and the acid addition salts thereof, which inhibit the growth of various microorganisms including drug-resistant bacterial isolants and which produce high blood levels through oral administration are produced by a biochemical reaction using the microorganisms of the genus Streptomyces which are selected for their newly-found ability to acylate the 3- and 4"-positions of 16-membered macrolide antibiotics; they are recovered from the reacted mixture by conventional methods for recovering macrolide antibiotics. The 3- and 4"-positions of 16-membered macrolide antibiotics in this specification mean the 3-position of 16-membered ring and the 4"-position of mycarose of the macrolide antibiotic, respectively.

(2) Characteristics of the Invention

Acylation of antibiotics is one of the practical methods for the production of new antibiotic species and their derivatives. Chemical synthesis is commonly employed for such acylation, but the acylation is liable to occur in a uniform fashion in many hydroxyl groups, whereby further reaction steps are required to obtain the desired product which is to be acylated at particular positions. Biochemical processes, on the other hand, facilitate selective acylation only at target positions due to the specificity of enzyme reactions and the yield is usually high. The present inventors have made a thorough investigation of one such biochemical conversion of macrolide antibiotics, especially of the acylation of macrolide antibiotics, and have found a number of microorganisms which are capable of specifically acylating the 3- and 4"-positions of 16-membered macrolide antibiotics. This is the first and novel finding of an enzyme reaction of the aforementioned type originating from microorganisms, and it is particularly applied to the production of new tylosin derivatives from tylosin.

(3) Description of the Prior Art

There has been no prior description regarding the tylosin compounds of the present invention, which are produced by the biochemical acylation of tylosin.

The chemical synthesis of tylosin acetyl ester and of acetylated tylosin is described in Japanese Patent (Kokoku) Showa No. 36-22649 entitled "Method for Producing Tylosin" as described in Examples 4 and 5. However the products are obviously different from the tylosin derivatives of the present invention, for the reason presented in the Detailed Description hereinbelow.

(4) Characteristics of the Process of the Invention.

The acylation of antibiotics is one of the practical methods for the production of new antibiotic species and derivatives. Chemical synthesis is commonly employed for such acylation, but the acylation is liable to occur in a uniform fashion throughout the hydroxyl groups of the compound, whereby extra measures and steps are required, e.g., the proper protection of some hydroxyl groups and of other functional residues, to obtain the desired product which is acylated at one particular position. A biochemical process, on the other hand, facilitates selective acylation due to the specificity of enzyme reaction and the yield is usually high. The present inventors have made a thorough investigation of such biochemical transformation of macrolide antibiotics, and have found that a number of microorganisms are capable of specifically and simultaneously acylating the 3- and 4"-positions of 16-membered macrolide antibiotics. A particular feature of this process is that a variety of acylated derivatives can be produced by the proper combination of the two components of the acylation systems produced by one organism, namely, the substrate antibiotics and the acyl donors, which is of substantial industrial merit.

There are two prior examples reported in connection with processes for the microbial acylation of 16-membered macrolide antibiotics, i.e., of spiramycin and YL-704. The process using spiramycin is presented in U.S. Pat. No. 2,943,024, entitled "Preparation of Spiramycin III", U.S. Pat. No. 2,943,025, entitled "Preparation of Spiramycin II", French Pat. No. 1,262,571, entitled "Transformation Biochimique de la Spiramycin I en Spiromycin II et III" and Japanese Patent (Kokoku) Showa No. 36-349, entitled "Process for Producing Spiramycin II, Spiramycin III and the Mixture Thereof." These patents practically deal with the same invention translated into different languages, describing processes which may be numerized as follows;

1. A spiramycin-producing organism, *Streptomyces ambofaciens* NRRL 2420, was cultivated in a culture medium to which spiramycin I, having a 3-hydroxyl group, was added and acylating agents, spiramcyin II, having a 3-acetyl group, and spiramycin III, having a 3-proionyl group, were produced.

2. The cells cultivated free of spiramycin and the acylating agents were suspended in a reaction medium, to which was added spiramycin I and the acylating agents. After incubation, spiramcyin II and III were produced.

3. In the fermentational production of spiramycins with the aforementioned organism, the addition of the acylating agents enhanced the production ratio of spiramycin II or III.

The process according to the present invention is clearly distinguishable in principle from the prior art process for microbially acylating spiramycin for the following reasons.

1. The prior art process uses an organism which is a direct producer of spiramycin, and the process is closely linked to antibiotic fermentation. The four favorable strains used in the present invention are non-producers of the desired antibiotic species, and this indicates that the process of the present invention is an enzymatic process in principle.

2. The substrate antibiotic used in the prior art process is limited to spiramycin I which is a direct product of the organism of the prior art process, while the process of the present invention can employ most of the 16-membered macrolide antibiotics, indicating the nonspecific nature of the reaction in terms of substrate specificity.

3. The prior art process can effect the conversion of only the 3-position of spiramycin I, while the process of the present invention can, if intended, carry out the simultaneous conversion of the 3- and 4"-positions with one organism. A much wider variety of products can be obtained with the proper combination of the substrate, the acyl donor and the reaction conditions. Also of significance is the simplicity of the process in converting the two functional positions simultaneously with one cell system.

With regard to YL-704, which is a family of leucomycins, Japanese Patent (Kokoku) Shown No. 49-13992 "Process for Producing an Antibiotic YL-704A₁" is presented. This patent indicates that an organism selected from the group consisting of *Strectomyces eurocidicus* NIHJ-267, *Streptomyces albireticuli* IFC-12737, *Streptomyces kitasatcensis* NRRL-2486 and *Streptomyces* sp. MCRL-0737 is cultivated in a medium containing "DHP compound", 4"-deacyl YL-704A₁, or the DHF compound and L-leucine and after its cultivation, YL-704A₁, which has an isovaleryl group at 4"-position of the DHP compound, is separated.

The processes of the present invention are also obviously different from that of the last mentioned patent, relating to YL-704A₁ production, in respects like those described in the case of the prior art spiramycin process, namely with respect to the organisms employed, the enzymatic nature of the processes of the present invention using enzyme system having no strict substrate specificity, the variety of products to be produced by the processes of the present invention and the fact that acylation at the 3- and 4"- positions can be effected simultaneously with one type of strain, all of which are of substantial industrial utility.

OBJECTS OF THE INVENTION

Accordingly, it is an object of this invention to provide a new compound having infection-control activities.

Another object of this invention is to provide a new pharmaceutical, a veterinary drug and a feed-additive composition and the methods for their use.

Still another object of this invention is to provide a new process for the acylation of at least one hydroxyl group at the 3- and 4"-positions of 16-membered macrolide antibiotics.

SUMMARY OF THE INVENTION

1. The present invention provided a new compound of the formula:

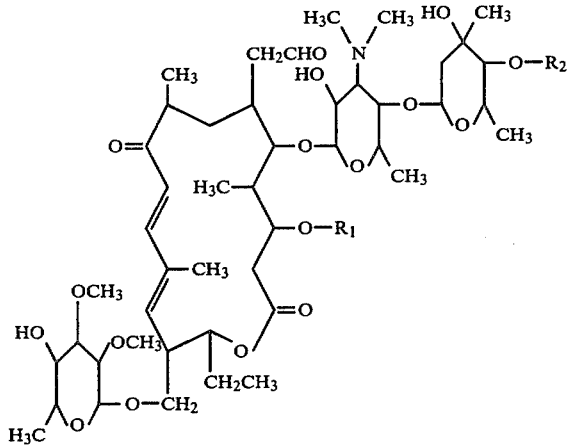

wherein $R_1$ is hydrogen, acetyl or propionyl and $R_2$ is hydrogen, n-butyryl or isovaleryl, the case where both $R_1$ and $R_2$ are hydrogen being excluded, and the non-toxic, pharmaceutically acceptable acid addition salts thereof, the new compounds being produced by acylating biochemically at least one of the 3- and 4"-hydroxyl groups of tylosin with the organism of the genus Streptomyces capable of exerting such acylation. The tylosin derivatives thus produced are recovered from the reacted mixture by conventional methods for recovering macrolide antibiotics.

The present invention thus provides new tylosin derivatives which (a) inhibit the growth of various micoorganisms including drug-resistant bacterial isolants, and (b) produce high blood levels through oral and enteric administration.

2. Other embodiments of the present invention provide a pharmaceutical, a veterinary drug, and a feed-additive composition for administration to humans and animals comprising such a compound in an amount sufficient to control infectious diseases caused by microorganisms.

3. Still other embodiments of the present invention provide a method for chemotherapeutically controlling infectious diseases caused by microorganisms in humans and animals by the administration of such a compound to the humans and animals in a dosage sufficient to control the infections.

4. The present invention further provides a process for producing 16-membered macrolide antibiotic compounds having at least one acyl group at the 3- and 4"-position, e.g., the tylosin derivatives having the above formula, which comprises culturing the organisms of the genus Streptomyces possessing the necessary acylation activity in a medium conventionally employed for culturing the organisms of this genus, performing such acylation reaction in a combination of the enzymatic sources, e.g., growing and non-growing cells of the cultured organism or the enzymatic preparations therefrom, the antibiotic substrate of 16-membered macrolide antibiotics having at least one hydroxyl group at the 3- and 4"-positions, e.g. tylosin, and the acyl-group donor of $C_2$–$C_5$ acyl compounds, e.g., acyl CoAs and their metabolic precursors, and recovering the acylated products from the reaction mixture by means of the conventionally employed method for recovering macrolide antibiotics.

DETAILED DESCRIPTION OF THE INVENTION

Figure 1:
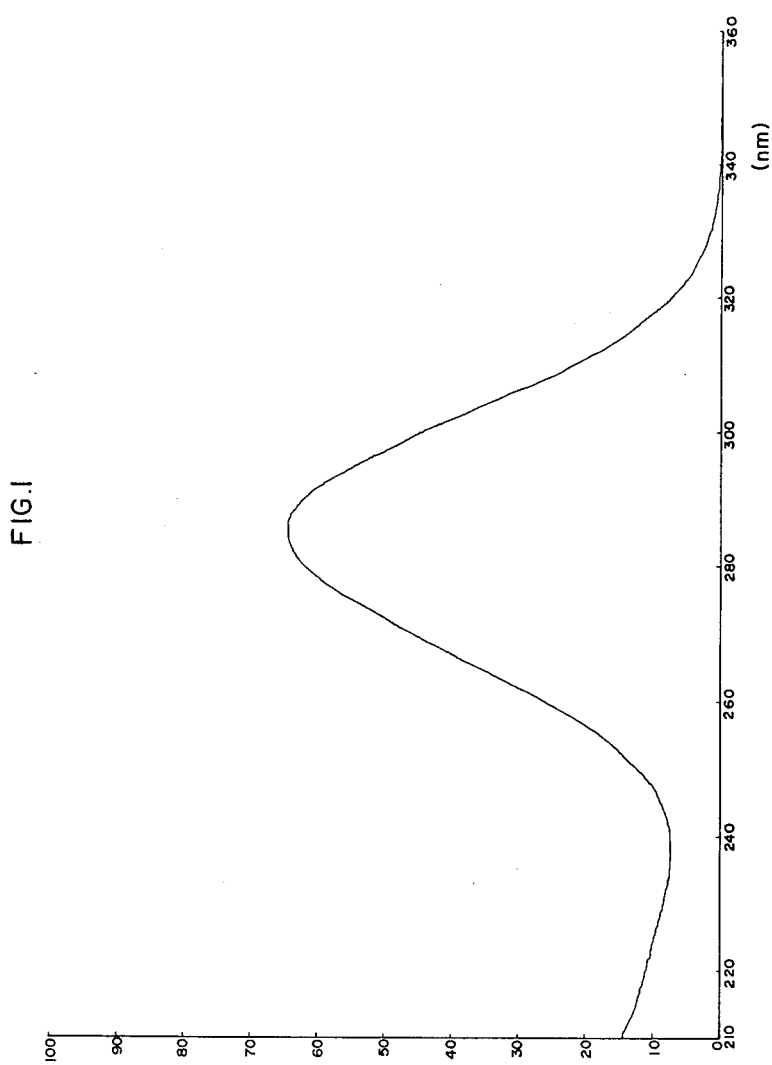
FIGS. 1 and 2 show the ultraviolet absorption spectra of 4"-n-butyryltylosin and 3-acetyl-4"-isovaleryltylosin, respectively.

This invention relates to new derivatives of macrolide antibiotics and their production. More particularly, it relates to new acylated derivatives of tylosin and to processes for the preparation thereof by the biochemical acylation of tylosin or its derivatives. In further detail, it relates to new derivatives of tylosin as shown in the following general formula I:

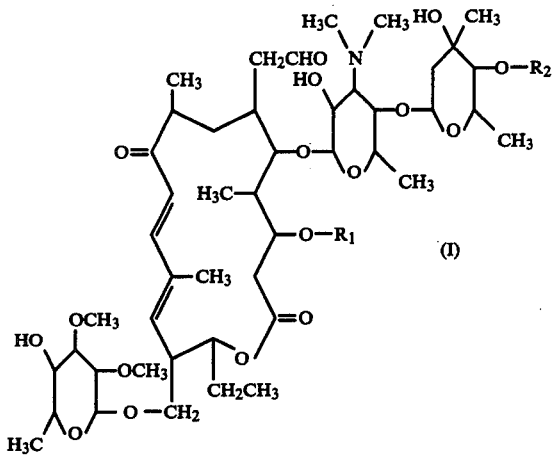

wherein $R_1$ is hydrogen, an acetyl group or a propionyl group and $R_2$ is hydrogen, an n-butyryl group or an isovaleryl group, the case where both $R_1$ and $R_2$ are hydrogen being excluded, which are produced by acylating tylosin or its derivatives of the formula I':

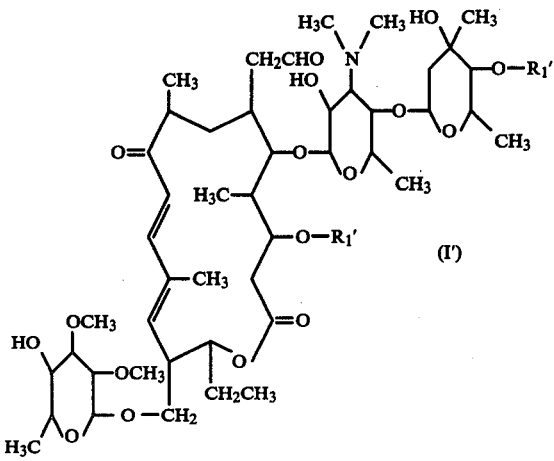

wherein $R_1'$ and $R_2'$ are both hydrogen or wherein either $R_1'$ or $R_2'$ is hydrogen and the other is an acyl group with a 2–5 carbon number, at least one of the hydroxyl at the 3- and 4"-position by the use of growing or resting cells, cell preparations or enzyme preparations of the microorganisms belonging to the genus Streptomyces which are capable of producing the enzyme for this acylation.

The acylation of antibiotics is one of the practical methods for the production of new antibiotic species and derivatives. Chemical processes are commonly employed in such acylation. However, the acylation is liable to occur in a uniform fashion, making necessary further steps, e.g., selective protection of functional residues, to obtain the desired product which is acylated at particular positions. Biochemical processes, on the other hand, cause selective acylation only at a target position due to the specificity of enzymatic reactions and the yield is usually high. The present inventors have made a thorough investigation of one such biochemical reaction, especially of the acylation of macrolide antibiotics, and have found that a number of microorganisms can specifically acylate both the 3-position and 4"-position of 16-membered macrolide antibiotics. The finding by the present inventors of the existence of this type of enzyme derived from microorganisms and enzymatic reactions is novel and the first of its kind. These reactions were studied further to establish biochemical conversion of macrolide antibiotics industrially and was particularly applied to the production of new tylosin derivatives from tylosin. The newly developed tylosin derivatives include 3-acetyltylosin, 3-acetyl-4"-n-butyryltylosin, 3-acetyl-4"-isovaleryltylosin, 3-propionyltylosin, 3-propionyl-4"-n-butyryltylosin, 3-propionyl-4"-isovaleryltylosin, 4"-n-butyryltylosin and 4"-isovaleryltylosin.

EXPERIMENT 1.

A medium of the following composition was prepared: soybean flour 40 g, glucose 50 g, yeast extract 1 g, $MgSO_4.7H_2O$ 0.5 g and $K_2HPO_4$ 0.5 g in 1000 ml of water (pH 7.0). 100 ml of the medium and placed in a 500 ml volume shaking culture flask, sterilized at 120° C. for 20 min., whereupon the medium was inoculated with Streptomyces thermotolerans ATCC 11416 which was then cultivated in the medium at 37° C. while the flask was shaken. After one days cultivation, when about half of the glucose was consumed, a solution of leucomycin $A_1$ was added to the medium in the proportion of 2 g/l and the reaction was continued for a further 6 hours. The reaction mixture obtained was cleared with centrifugation, adjusted to pH 8.5 by dilute sodium hydroxide solution, and extracted with an equal volume of ethyl acetate. The extract was concentrated to about one third of its original volume under reduced pressure and a portion was spotted on a thin-layer plate of silica gel (Merck Co.). It was then developed by a solvent mixture of n-hexane:acetone:methanol:benzene:ethyl acetate (30:10:8:25:20), completely dried and then dipped in 10% sulfuric acid and heated. Two spots were detected having Rf values of about 0.50 and 0.65 which were attributed to leucomycin $A_1$ and leucomycin $A_3$ (3-acetylleucomycin $A_1$), respectively, by comparison with authentic samples.

EXPERIMENT 2.

The cells grown in Experiment 1 (just before the addition of the antibiotics) were collected by centrifugation, rinsed once with 0.05 N phosphate buffer solution of a pH of 6.5 and resuspended in the same buffer solution with added glucose in a concentration of 2 g/liter. The concentration of cells in the buffer solution was about 10 g dry matter/liter. Then, leucomycin V and L-leucine were added in concentrations of 0.5 g/liter and 1 g/liter, respectively, and aerobial incubation was conducted under conditions similar to those for cell cultivation. Three hours later, the reaction was terminated, which was followed by the procedures as in Experiment 1. On a thin-layer chromatography plate, two spots emerged having Rf value of about 0.3 and 0.65, respectively, and which was identified as the substrate, leucomycin V, and the product, leucomycin A$_3$ (3-acetyl-4"-isovalerylleucomycin V).

EXPERIMENT 3.

Cells obtained and rinsed as in Experiment 2 were resuspended in a small amount of the aforementioned phosphate buffer solution and homogenized by the use of a French Press, from which a supernatant fluid was obtained by centrifugation at 3000×G for 10 min. To a diluted solution of the supernatant, leucomycin U and isovaleryl Coenzyme A (hereinafter Coenzyme A is abbreviated as CoA) were each added in concentration of 0.2 g/liter and the reaction occured as in Experiment 2. The formation of leucomycin A$_3$ (4"-isovalerylleucomycin U) was confirmed by a thin-layer chromatogram.

As preliminarily outlined in Experiments 1–3, the acylation reaction of macrolide antibiotics according to the present invention required the presence of and contact with three basic components, namely, an enzyme-active preparation for the acylation in the form of cells or enzyme preparations, a 16-membered macrolide antibiotic as the substrate, e.g. tylosin, and an acyl donor. The following description embodies in detail the execution of the present invention.

Organisms possessing the necessary acylation activity are selected from stock culture deposits and also from wild isolants by testing the organisms for that acylating activity. Organisms possessing strong acylating activity and preferably employed in this invention belong to the genus Streptomyces and exemplary strains among the deposited cultures are:

*Streptomyces thermotolerans* ATCC 11416
Streptomyces fungicidicus subsp. *espinomyceticus*

|  | ATCC 21574 |
|---|---|
| *Streptomyces hygroscepicus* | ATCC 21582 |
| *Streptomyces mycarofaciens* | ATCC 21454 |

The variants and the mutants obtained naturally or artificially from organisms possessing the necessary acylation activity are also used in the present invention. For instance, mutants possessing enhanced acylating activity can be derived by conventionally used techniques for microbial mutation and selection.

In the present invention these organisms are cultivated by employing the general procedure used for the cultivation of strains of the genus Streptomyces but suitable conditions should be set up so as to get full acylation potency for the aforementioned enzymatic activity. The culture medium preferably contains carbon sources such as glucose, maltose, sucrose, starch or malt-syrup, alcohols such as ethanol and glycerin, oils, fats and waxes of plant or animal origin, organic acids such as acetic acid and citric acid and the salts thereof, but other assimilable components which serve as such carbon sources are employable. These compounds are used singly or in combinations of two or more in a concentration of 0.5–10 g/dl generally and preferably of 2–6 g/dl, depending upon the kind of compounds employed. The nitrogen sources preferably employed are protein-rich organic compounds of animal, plant or microbial origin such as casein, peptone, floured products prepared from soybean, corn, cotton seed and preparations from yeast and bacteria, and various inorganic compounds conventionally used as a nitrogen source such as ammonium salts. Other nitrogen-rich compounds which can be assimilated by the organisms are also employable. These nitrogen sources are used singly or in combinations of two or more in the medium in a concentration of 0.1–10 g/dl. With organic materials the preferred concentration is 1–6 g/dl, and with inorganic compounds, it is set lower. The medium also contains inorganic salts such as phosphates, magnesium salts, mineral salts and growth promoting materials such as yeast extract, meat extract and vitamins or vitamin-rich materials. They are used in concentrations of 0.01–0.5 g/dl, depending upon the kind of organism and the medium composition employed.

The cultivation of the organisms is carried out aerobically by means of aeration and agitation. The pH of the medium is maintained in the range of 4.5–9.0, and preferably from 6.0–8.0. Cultivation temperature is maintained at 20°–45° C., the preferred temperature being 20°–35° C. with general Streptomyces strains and 30°–40° C. particularly with *Streptomyces thermotolerans*. The acylating activity of 16-membered macrolide antibiotics by the organisms according to the present invention is produced at an early growing phase and is preserved although growth has ceased. Particularly high specific activity of the acylation of the 3-hydroxyl group is found in cells of early to late growing phases and that for the acylation of 4"-hydroxyl group is found from the late growing phase to the post-growing stage.

As shown in Experiments 1–3, the acylation can be performed with cells under growth-associated conditions or at rest either in the cultured medium or after separation from the medium, or with various forms of enzymatic preparations, e.g., dried cells or cell homogenate, the supernatant solution being obtained from homogenate and enzyme preparations. An immobilized enzymatic preparation such as that fixed in an acrylamide polymer is also employable. As the result of studies on the nature of the acylation, it has been revealed that two enzyme systems are independently included in such acylation. They are macrolide 3-acyl transferase and macrolide 4"-acyl transferase, as tentatively named by the present inventors, and which transfer acyl groups to the 3- and 4"-hydroxyl groups, respectively, of 16-membered macrolide antibiotics. These enzyme systems catalyze the transfer in a non-specific fashion in terms of the kind of acyl group, however, they have respective preferences for particular acyl group such that macrolide 3-acyl transferase preferably transfers acetyl group, propionyl group and n-butyryl group in that order, while macrolide 4"-acyl transferase transfers isovaleryl group, n-butyryl group and propionyl group in that order.

The acyl donor employed in the acylating reaction of this invention includes acyl CoAs which serves as a direct donor of the acyl group to be incorporated, and the precursor compounds for such acyl CoA from which the respective acyl CoA are produced in the cell through cell metabolism. The acyl CoA preferably employed includes acetyl CoA, propionyl CoA, n-butyryl CoA and isovaleryl CoA, and their precursor compounds include organic acids such as acetic acid, propionic acid, n-butyric acid and isovalerylic acid, and the salts thereof, such as potassium, sodium and ammonium salts etc., the esters thereof such as, methanol and ethanol esters, etc. and the amides thereof. Also included are amino acids such as α-amino-butyric acid, norvaline, L-leucine, and keto acids such as α-ketobutyric acid and α-ketovalerylic acid.

In general, the acyl CoAs are used and added to the reaction medium when the reaction is conducted with an enzymatic system of poor ability to generate respective acyl CoA from CoA and the acyl precursors. On the other hand, acyl precursor compounds are used when the system for regenerating the concerned acyl CoA e.g., cell growing conditions and the like, is fully operative. The amount of acyl donors added to the reaction medium is usually equivalent to or approximately equivalent to the antibiotic substrate in the case of acyl CoA, and in higher mole ratios, e.g., 3–10 mole ratio, in the case of precursor compounds. Living cells can produce acetyl CoA from carbon sources through their metabolic cycle; hence, if a sufficient quantity of carbon source is present in the reaction with living cells, acetylation usually proceeds by the use of endogenously-formed acetyl CoA. Likewise, in such a reaction system, since propionyl CoA and other CoAs are produced in far smaller amounts then acetyl CoA, only a small amount of such acylated products are noted in the reacted mixture. In the case where acyl CoAs is used in the reaction, when the reaction is completed, CoA can be recovered from the reaction medium by conventionally-employed methods for CoA isolation and the recovered CoA can be reused for the synthesis of acyl CoA.

The substrate antibiotics for the acylation are added to the reaction mixture in such forms as a water solution, a solution in a weakly acidic aqueous fluid and solutions in solvents which exert little adverse effect on the reaction, e.g., methanol and ethanol, or in the forms of aqueous solvent mixtures, suspensions, slurries and fine powders. A concentration of antibiotic compounds in the reaction mixture of 0.1–50 g/liter, preferably 0.5–30 g/liter is employed. The antibiotics employable in this invention are those having a 16-membered macrolide ring, e.g., leucomycins, maridomycins, spiramycins, angolamycin, tylosin, carbomycin A and carbomycin B, in which at least one group at 3- and 4"-position is hydroxyl naturally or is made hydroxyl by chemical or biochemical methods.

The chemical and physical conditions in the acylating reaction are practically similar to those for cultivation of the cells of each of the organisms used, which would also be favored conditions for the enzymatic reactions pertinent to such particular cells. Reaction temperature is 25°–43° C., preferably 28°–40° C., and pH is maintained in the range of 5.0–8.5, preferably at 5.5–8.0 for the acylation of the 3-position and 6.5–8.5 for acylation of the 4"-position. The use of an appropriate buffer solution is desired for the maintenance of the intended pH value in the case of reactions without cell growing. The buffer solutions conventionally employed for general enzymatic reactions such as phosphate buffer solution, citrate buffer solution, etc. are employable; however, the use of acetate buffers or those containing acetyl groups in their compositions should be confined just to acetylation reactions. The reaction period is usually 30 minutes to 10 hours.

The following descriptions further illustrate some favorably-conducted processes of the said acylation to produce the tylosin derivatives of the present invention in particular:

(1) 4"-n-butyryltylosin

The aforementioned organisms are grown in a medium containing restricted concentrations of carbon and nitrogen sources, and when the carbon sources are almost entirely consumed, tylosin is added to the broth in an amount exceeding the acylation activity of the 3-position of the cells together with n-butyryl CoA or its precursors.

The reaction is carried out under practically the same conditions as in cell cultivation. Part of the added substrate is acetylated to form 3-acetyltylosin, while the other part remains unacetylated. Meanwhile, the concurrent butyrylation of the 4"-hydroxyl group proceeds, resulting in the formation of 4"-n-butyryltylosin and a smaller amount of 3-acetyl-4"-n-butyryltylosin, from which the former product is isolated.

(2) 4"-isovaleryltylosin

In an acylation reaction conducted in a manner similar to (1), the use of isovaleryl CoA or its percursors as the acyl donor causes the formation of 4"-isovaleryltylosin in the reaction fluid.

(3) 3-acetyltylosin

For the production of 3-acetyltylosin, the organism, for instance, *Streptomycea thermotolerans* ATCC 11416, is grown in a medium containing a plentiful quantity of carbon and nitrogen sources. When maximum growth has been reached and the carbon sources still remain in substantial amounts, tylosin is added to the medium in a limited amount not exceeding the acetylating activity of the cells. Vigorous agitation and aeration are maintained throughout the reaction accompanied by cell growth and the acetylation is carried out by the use of acetyl CoA reproduced in the cells, yielding 3-acetyltylosin.

(4) 3-acetyl-4"-n-butyryltylosin (i) The aforementioned organisms are grown in a medium containing a rather restricted amount of carbon source and a balanced amount of nitrogen source until the concentration of carbon source decreases to the bottom level, at which time tylosin or 3-acetyltylosin is added in an amount not exceeding the acylating capability of the cells, together with n-butyryl CoA or its precursor compounds as the n-butyryl group donor. The reaction is carried out until the antibiotic substrate is fully acylated, and the product, 3-acetyl-4"-n-butyryltylosin, is then isolated.

(ii) Using 4"-n-butyryltylosin as the substrate, the reaction is effected in practically the same manner as in (3) for the production of 3-acetyltylosin with acetylation of the 3-hydroxyl group, i.e. 3-acetyl-4"-n-butyryltylosin is produced.

(5) 3-Acetyl-4"-isovaleryltylosin

For the production of the 3-acetyl-4"-isovaleryltylosin, practically the same methods as in (4) (i) and (ii) are employable, in which isovaleryl CoA or its precursor compounds are used as the acyl donor in (i) and 4"-isovaleryltylosin as the substrate in (ii).

(6) 3-propionyltylosin

For the production of 3-propionyltylosin, the aforementioned organisms are grown in a medium containing a restricted amount of carbon source and a plentiful amount of nitrogen source. When the carbon source is almost completely consumed, the substrate tylosin is added to the cultured broth in an amount not exceeding the propionylation capability of the cells, together with propionylating donors, i.e., propionyl CoA or its precursors. The reaction is carried out for full propionylation.

(7) 3-propionyl-4"-n-butyryltylosin 3-propionyl-4"-n-butyryltylosin can be produced in two steps. First, 3-propionyltylosin is produced from tylosin by the method in (6).

When the first reaction is almost completed, the n-butyryl donor, i.e., n-butyryl CoA or its precursor, and a small amount of carbon sources, if necessary, are added to the medium and aerobic reaction is carried out. 3-propionyl-4''-n-butyryltyrosin is thus obtained.

Needless to say, it can also be produced in one step by adding 3-propionyltylosin as the substrate to the grown cell mixture together with the acyl donors.

(8) 3-propionyl-4''-isovaleryltylosin

In a manner similar to (7), the use of an isovaleryl donor, i.e., isovaleryl CoA or its precursor compound, in place of n-butyryl donor, leads to the formation of 3-propionyl-4''-isovaleryltylosin.

The acylated compounds produced from the 16-membered macrolide antibiotics, according to this invention, can be isolated, purified and formulated through the application of the methods generally employed in the production of each 16-membered macrolide antibiotic.

For the isolation of tylosin derivatives, if necessary, after weakly acidifying the reaction mixture is separated from the cells and other insoluble particulates by such methods as filtration and centrifugation. The clear solution is then adjusted to form a neutral to slightly alkaline pH and extracted with water-immiscible solvents, e.g., ethyl acetate, toluene and benzene, which are conventionally used for the extraction of macrolide antibiotics. For the further removal of impurities derived from the reaction mixture, the extract is mixed with acidified water or buffer solution to transfer the tylosin derivatives in an aqueous layer, to which the above extraction by the aforementioned solvents is repeated.

Since a series of tylosin derivatives are present in the extract, they are separated by various differentiation methods for macrolide antibiotics. In the case where their partition coefficients in relation to water and organic solvents are widely differing, methods such as counter current extraction and separating extraction are employed. On the other hand, if the coefficients are marginal, chromatographical methods, using silica gel, ion-exchange resin etc. are applied according to the type of derivative species contained therein.

The derivatives are obtained in a solid form by the ordinary concentration of such antibiotic solutions until they become dry or by crystallization. For crystallizing the derivatives in a highly pure form, the crude preparation is dissolved in organic solvents such as acetone and methanol, and then the solution is gradiently added to a liquid such as water and n-hexane in which the derivative is hardly soluble. Crystallization can also be carried out with solvents such as ethyl ether and a mixture of ethyl ether and isopropyl ether which exhibits a low solubility for the derivatives. 3-acetyltylosin is easily crystallized from benzene and toluene. The crystals collected are dried to produce a white crystalline powder.

Eight tylosin derivatives developed by this invention, i.e., 3-acetyltylosin, 3-acetyl-4''-n-butyryltylosin, 3-acetyl-4''-isovaleryltylosin, 3-propionyltylosin, 3-propionyl-4''-n-butyryltylosin, 3-propionyl-4''-isovaleryltylosin, 4''-n-butyryltylosin and 4''-isovaleryltylosin were proved to be new compounds from results of studies on their physicochemical properties, chemical structures, etc. The physicochemical analysis and determinations included elementary analysis, melting point, specific rotatory power, ultraviolet spectrum, infrared spectrum, magnetic nuclear resonance (NMR), $C^{13}$-NMR, mass spectrum (chemical ionization), the release of organic acids under alkaline conditions (gas chromatographical detection), solubility in solvents, color development reaction, basicity of the compounds, appearance and crystalline form. The molecular weight was obtained as QM+ (Quasi Molecular ion) by chemically-ionized mass spectra analysis. These results are shown in Table 1 and FIGS. 1–23 in which:

(1) detection of organic acids by gas chromatography the solutions were prepared in 0.5 N KOH-ethanol solution, treated at 70°–75° C. for 20 min. and applied to analysis, (2) the crystals obtained from the solvents in (13) were used for the tests in (1)–(12), and (3) the molecular weights were obtained as QM+ from chemical ionizing mass spectra using $CH_4$ as reactant gas.

Table 1.

Figure 2:
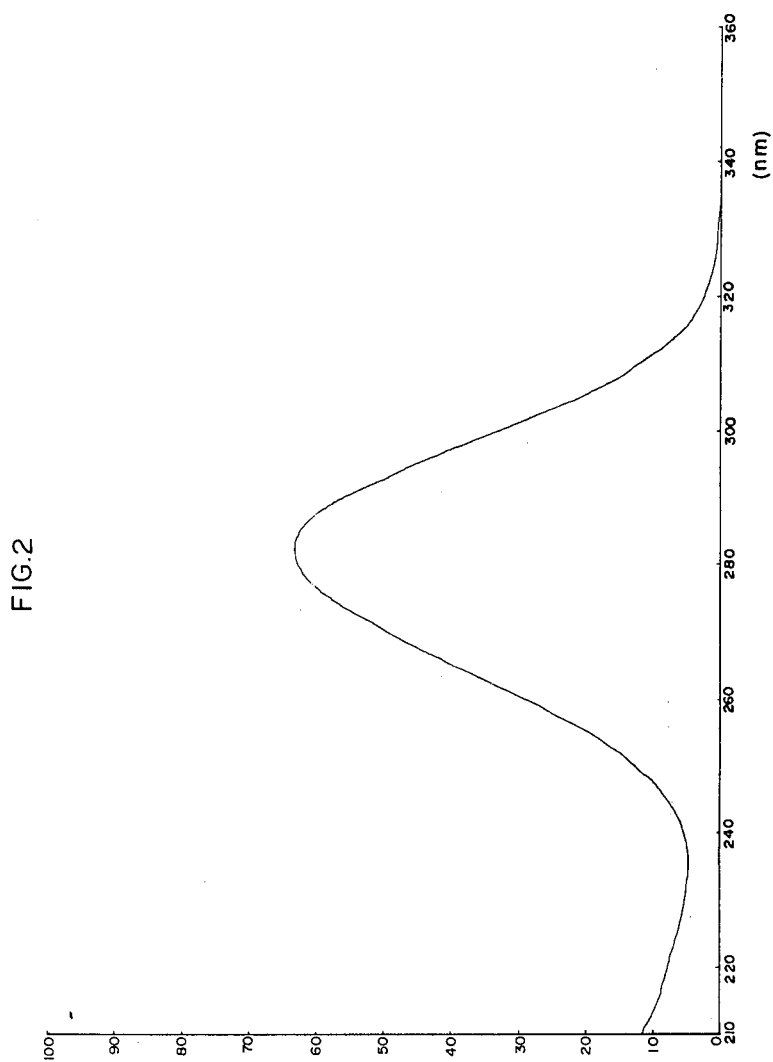

| | | | | |
|---|---|---|---|---|
| Physico-chemical Properties of Tylosin Derivatives | | | | |
| compounds analysis | 3-acetyltylosin | 3-acetyl-4''-n-butyryltylosin | 3-acetyl-4''-isovaleryltylosin | 3-propionyltylosin |
| (1) appearance | | white crystalline powders | | |
| (2) elementary analysis (calculated value) (%) | C:60.25(60.17) H:8.27(8.31) O:29.98(30.06) N:1.50(1.46) | C:60.70(60.75) H:8.39(8.33) O:29.51(29.56) N:1.40(1.36) | C:61.05(61.08) H:8.33(8.41) O:29.23(29.17) N:1.39(1.34) | C:60.45(60.54) H:8.46(8.40) O:29.59(29.62) N:1.50(1.44) |
| (3) molecular weight Mass spectroscopy | 958 | 1028 | 1042 | 972 |
| (4) melting point | 214°–219° C. | 177°–181° C. | 180°–184° C. | 187°–192° C. |
| (5) specific rotatory power $[\alpha]_D^{24}$ (1%) C=methanol solution | −33.9 | −31.1 | −34.3 | −31.2 |
| (6) ultraviolet absorption spectra $E_{1cm}^{1\%}$ | $\lambda_{max}^{MeOH}$ 282nm 235 | $\lambda_{max}^{EtOH}$ 282nm 240 | $\lambda_{max}^{EtOH}$ 282nm 222 FIG. 2 | $\lambda_{max}^{EtOH}$ 282nm 236 |
| compounds analysis | 3-propionyl-4''-n-butyryltylosin | 3-propionyl-4''-isovaleryltylosin | 4''-n-butyryltylosin | 4''-isovaleryltylosin |
| (1) appearance | | white crystalline powders | | |
| (2) elementary analysis (calculated value) (%) | C:61.05(61.08) H:8.37(8.41) O:29.25(29.17) N:1.33(1.34) | C:61.53(61.40) H:8.46(8.40) O:28.70(28.78) N:1.31(1.33) | C:61.03(60.90) H:8.55(8.48) O:28.94(29.20) N:1.48(1.42) | C:61.33(61.24) H:8.65(8.57) O:28.56(28.79) N:1.46(1.40) |

Table 1.-continued
Physico-chemical Properties of Tylosin Derivatives

| | | | | |
|---|---|---|---|---|
| (3) molecular weight Mass spectroscopy | 1042 | 1056 | 986 | 1000 |
| (4) melting point | 182°–188° C. | 180°–186° C. | 147°–151° C. | 154°–157° C. |
| (5) specific rotatory power $[\alpha]_D^{24}$ (1%) C=methanol solution | −35.2 | −33.2 | −53.4 | −50.8 |
| (6) ultraviolet absorption spectra $E_{1cm}^{1\%}$ | $\lambda_{max}^{EtOH}$ 282nm 210 | $\lambda_{max}^{EtOH}$ 282nm 227 | $\lambda_{max}^{EtOH}$ 285nm 214 FIG. 1 | $\lambda_{max}^{EtOH}$ 284nm 217 |

Figure 3:
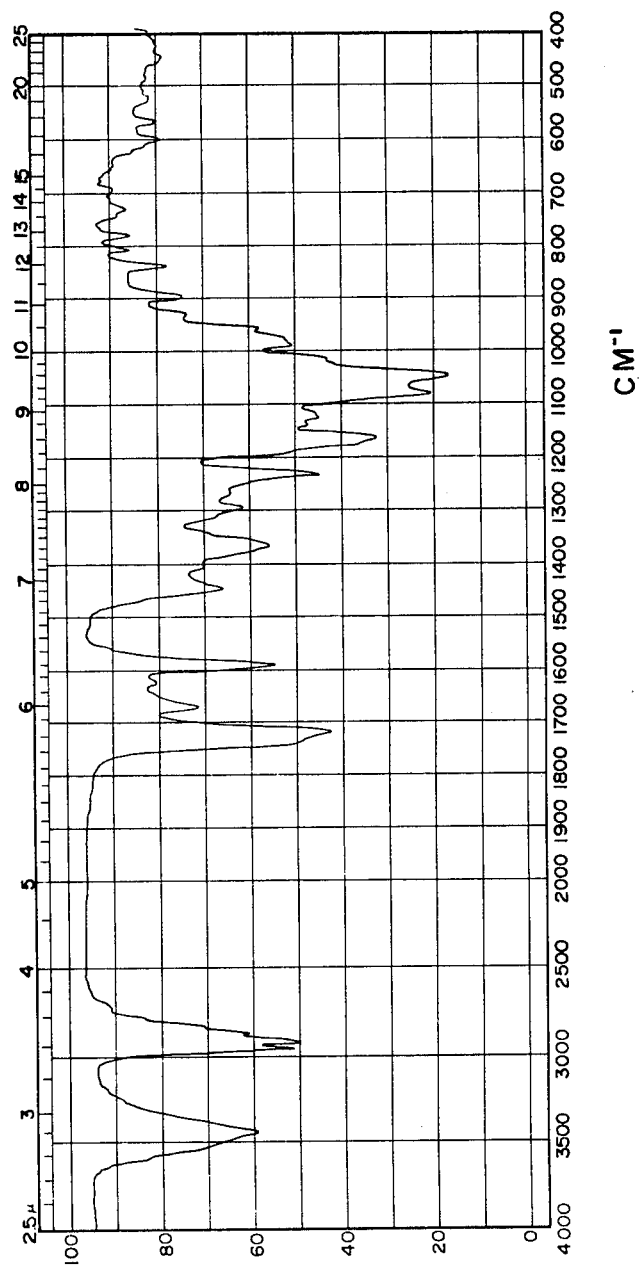
FIGS. 3,4,5,6,7,8,9 and 10 show the infrared absorption spectra of 3-acetyltylosin, 3-acetyl-4"-n-butyryltylosin, 3-acetyl-4"-isovaleryltylosin, 3-propionyltylosin, 3-propionyl-4"-n-butyryltylosin, 3-propionyl-4"-isovaleryltylosin, 4"-n-butyryltylosin and 4"-isovaleryltylosin, respectively.
Figure 4:
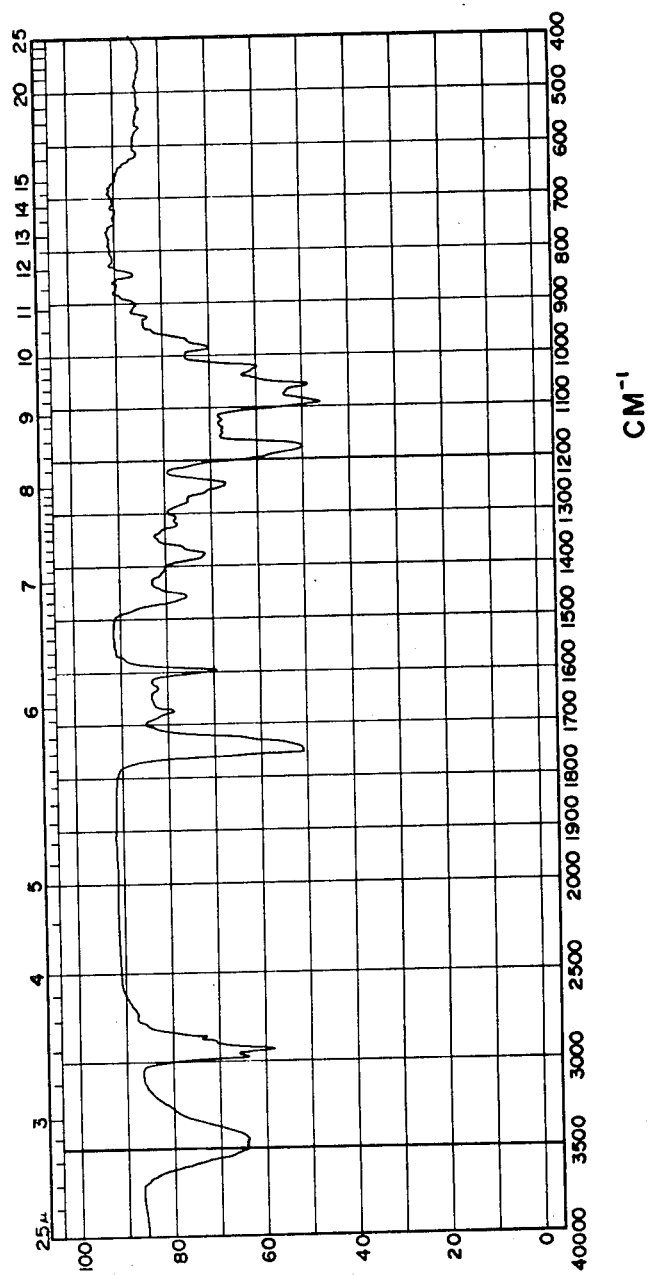
Figure 5:
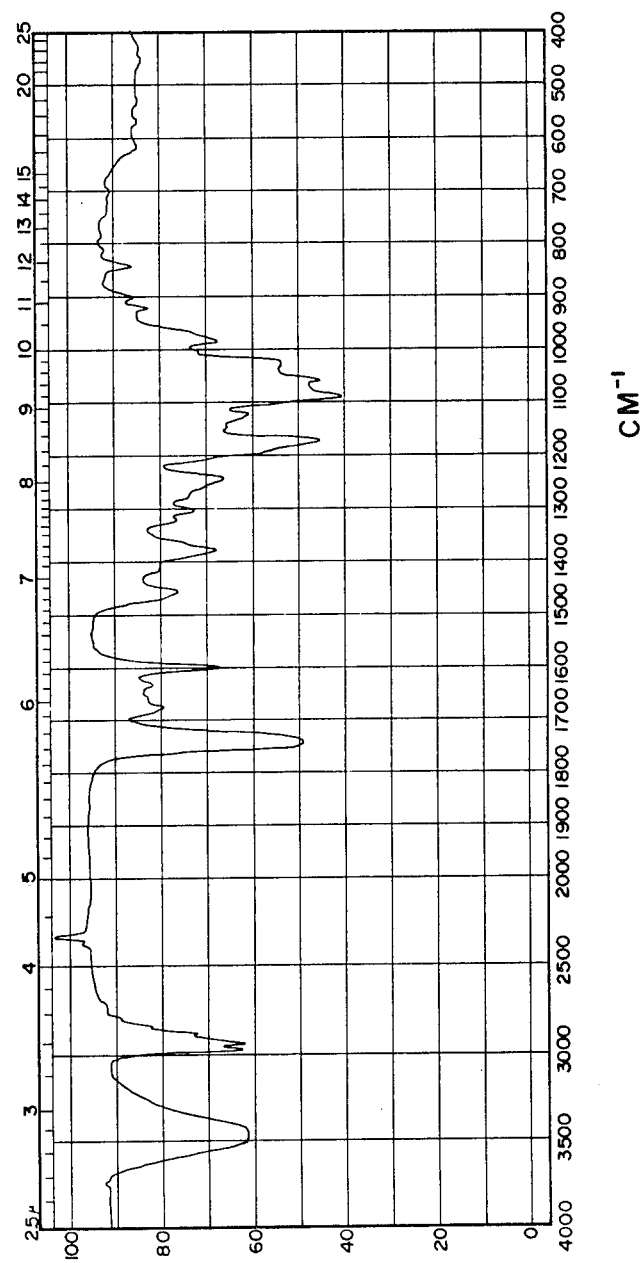
Figure 6:
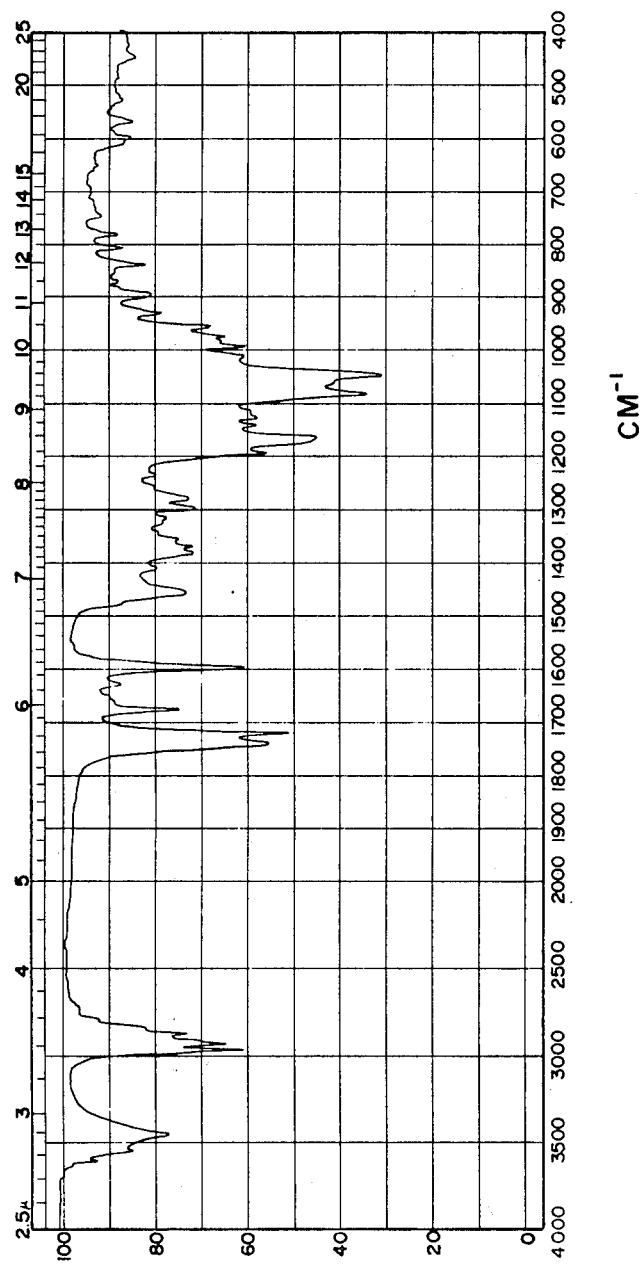
Figure 11:
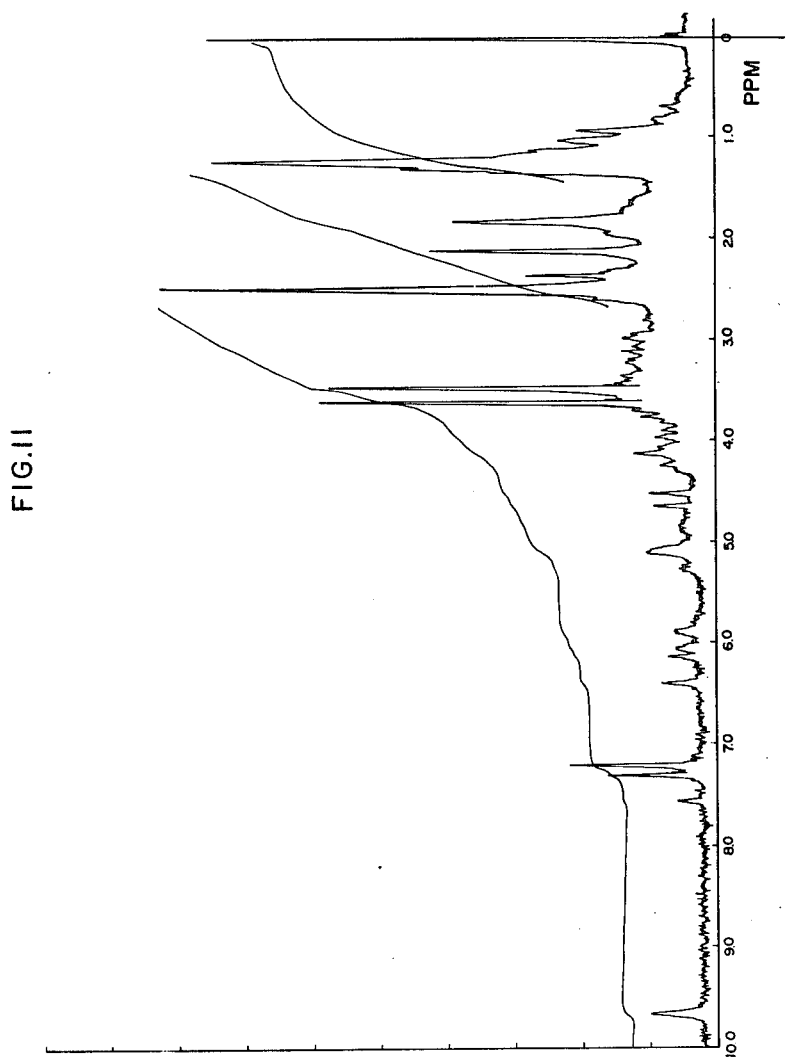
FIGS. 11,12,13,14,15,16,17 and 18 are the NMR spectra (CDCl₃) of the aformentioned, respective compounds presented in the same order as the infrared absorption spectra.
Figure 12:
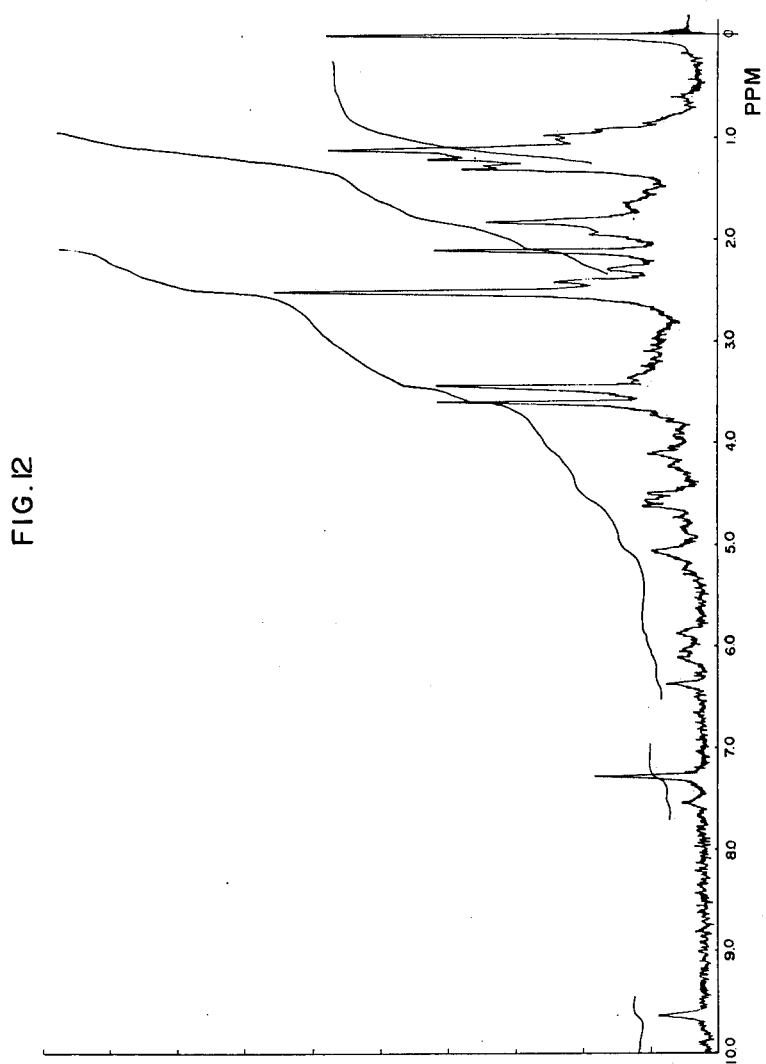
Figure 13:
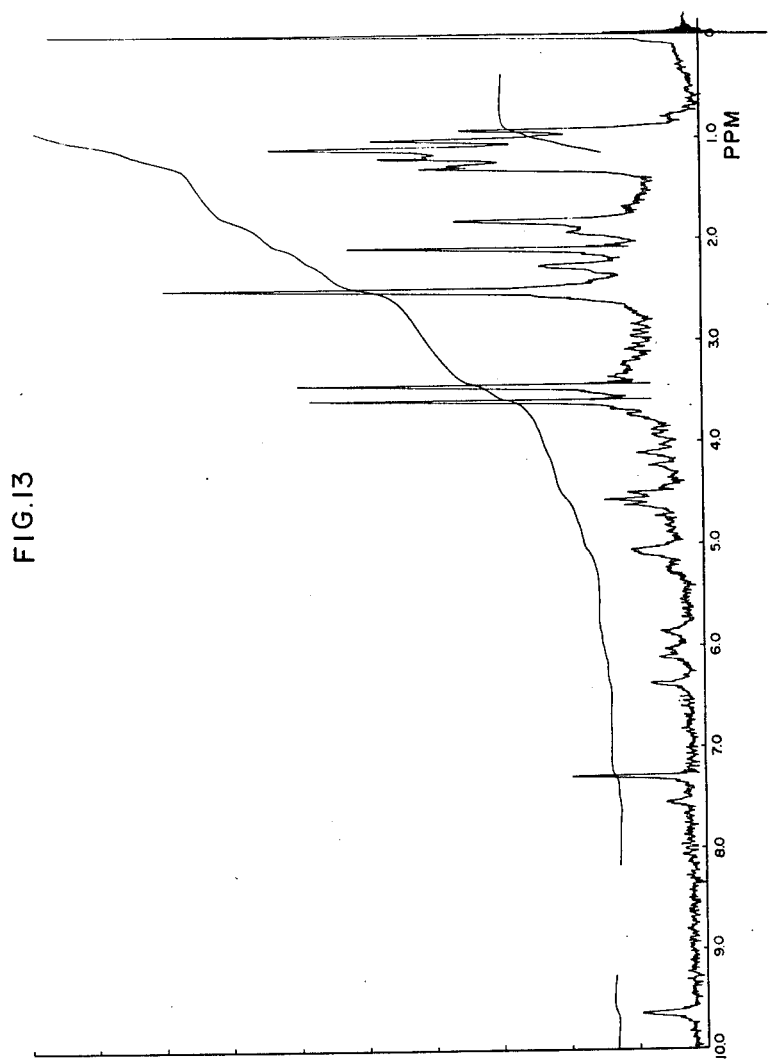
Figure 14:
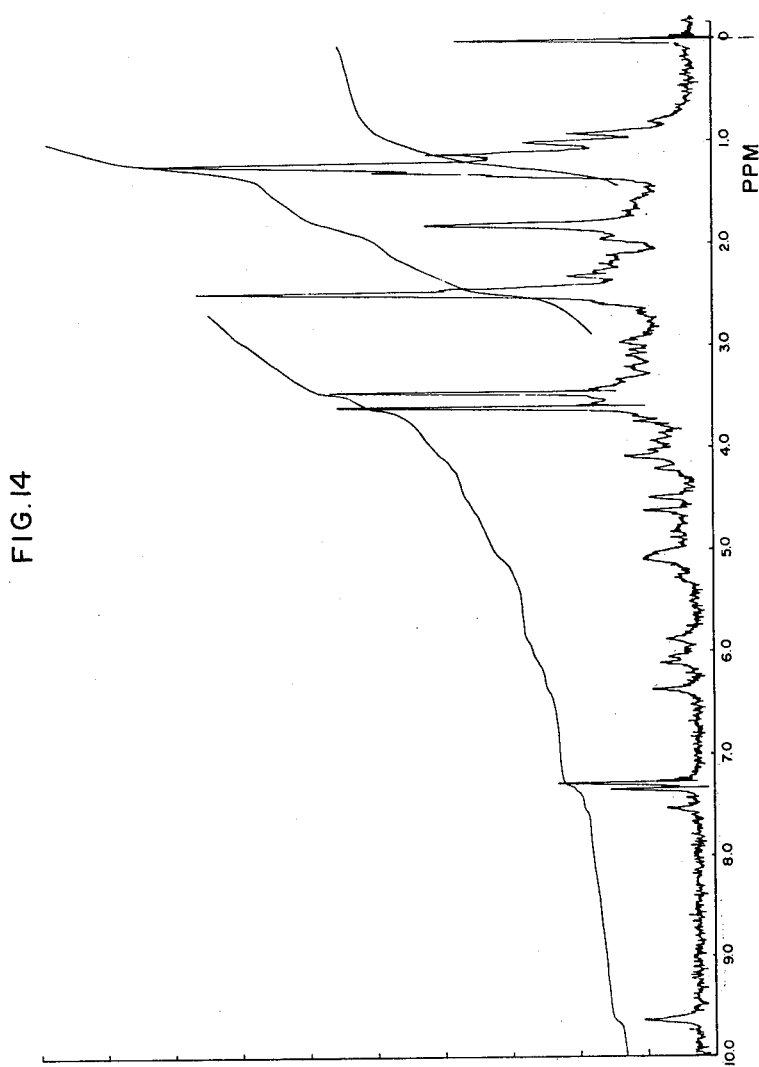

| compound analysis | 3-acetyltylosin | 3-acetyl-4"-n-butyryltylosin | 3-acetyl-4"-isovaleryltylosin | 3-propionyltylosin |
|---|---|---|---|---|
| (7) infrared absorption spectra (KBr pellet) (cm$^{-1}$) | 3440, 2960, 2920, 2865, 2835, 2790, 2710, 1733, 1716, 1667, 1620, 1588, 1443, 1403, 1360, 1295, 1265, 1235, 1159, 1138, 1123, 1078, 1043, 1010, 987, 953, 925, 893, 838, | 3500–3440, 2980, 2940, 2890, 2860, 2800, 2730, 1750, 1675, 1631, 1597, 1456, 1382, 1376, 1360, 1320, 1305, 1280, 1260, 1244, 1174, 1089, 1057, 1020, 984, 968, 925, 902, 849 | 3510–3440, 2980, 2940, 2885, 2845, 2800, 2720, 1741, 1676, 1632, 1598, 1457, 1418, 1377, 1320, 1303, 1277, 1242, 1172, 1147, 1122, 1088, 1057, 1030, 1000, 932, 921, 900, 842, | 3460, 2980, 2945, 2880, 2850, 2800, 2730, 1744, 1724, 1680, 1633, 1630, 1459, 1417, 1383, 1374, 1360, 1345, 1327, 1319, 1301, 1281, 1259, 1168, 1145, 1133, 1120, 1087, 1067, 1053, 1018, 988, 988, 980, 960, 934, 901, 843, 810, 784 |
| | FIG. 3 | FIG. 4 | FIG. 5 | FIG. 6 |
| (8) NMR (CDCl$_3$) 60MHz | FIG. 11 | FIG. 12 | FIG. 13 | FIG. 14 |
| (9) organic acids detected by gas chromatography | acetic acid | acetic acid and n-butyric acid | acetic acid and isovaleric acid | propionic acid |

Figure 7:
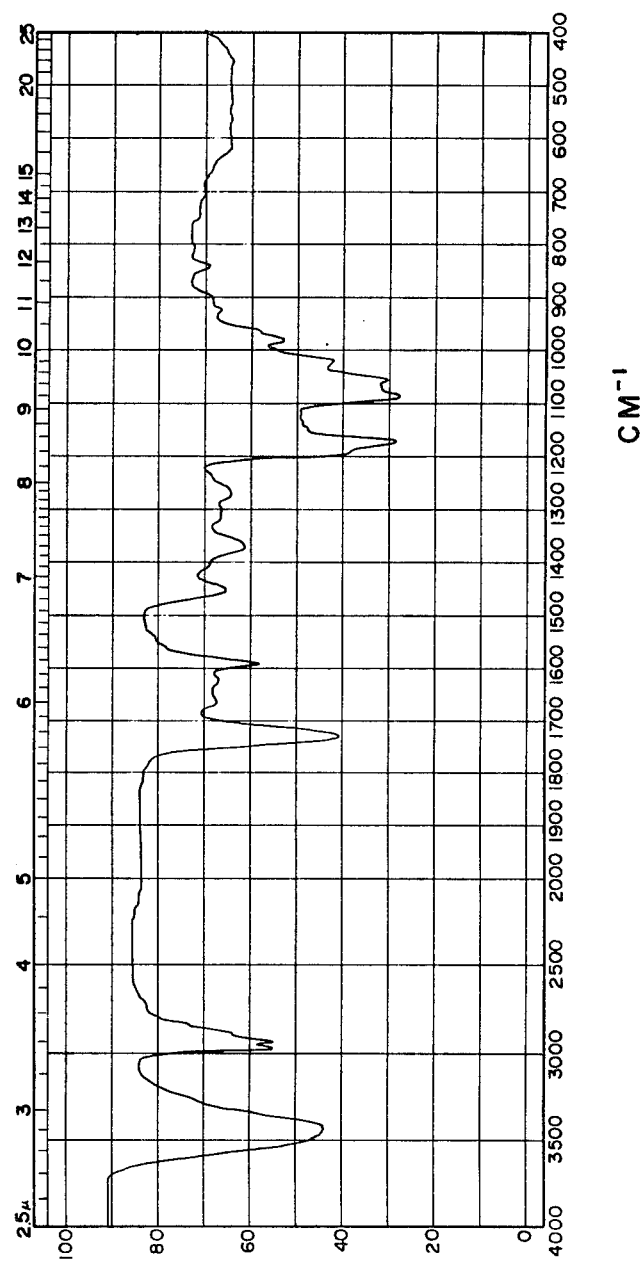
Figure 8:
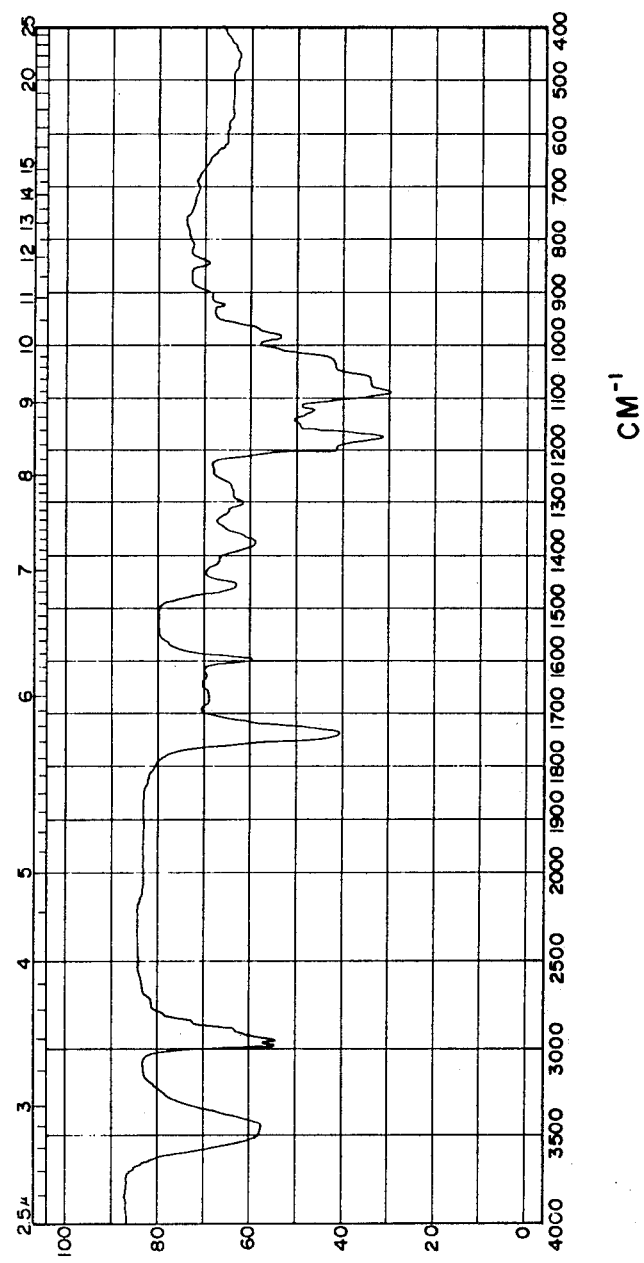
Figure 9:
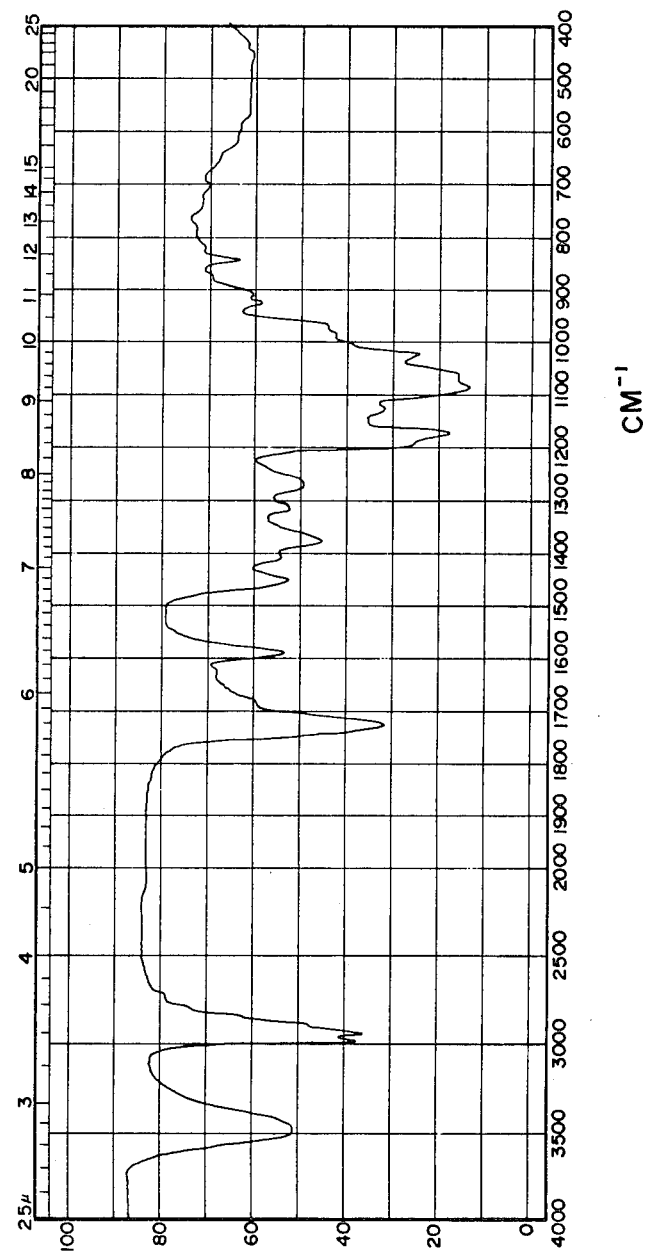
Figure 10:
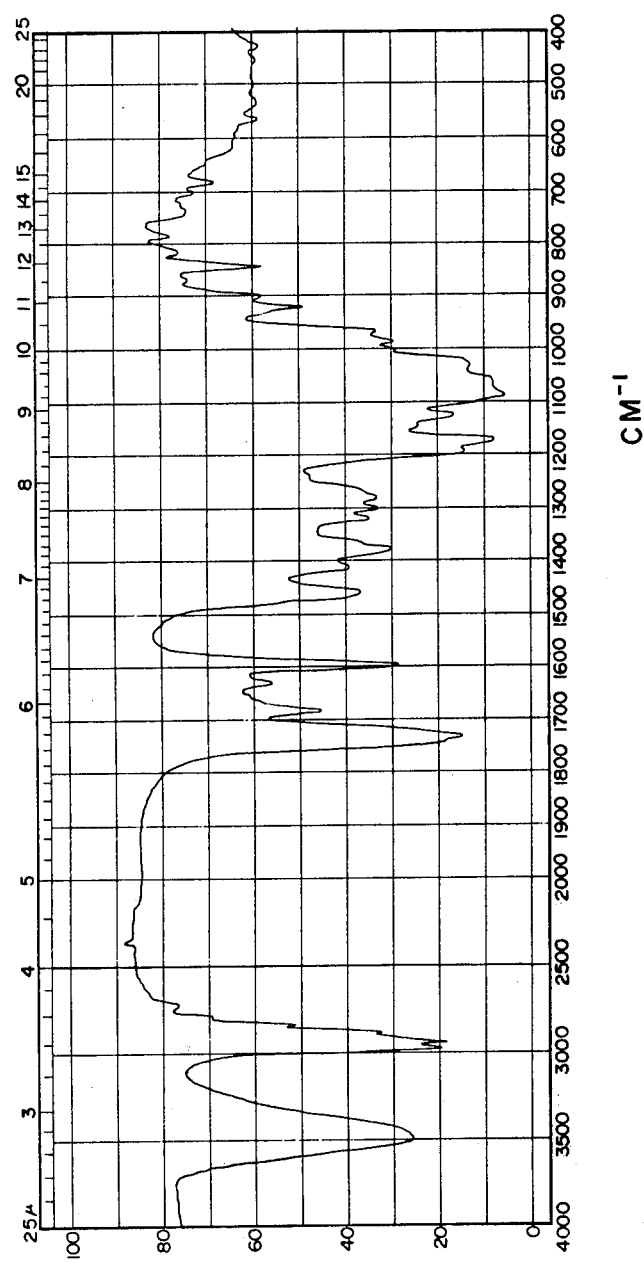
Figure 15:
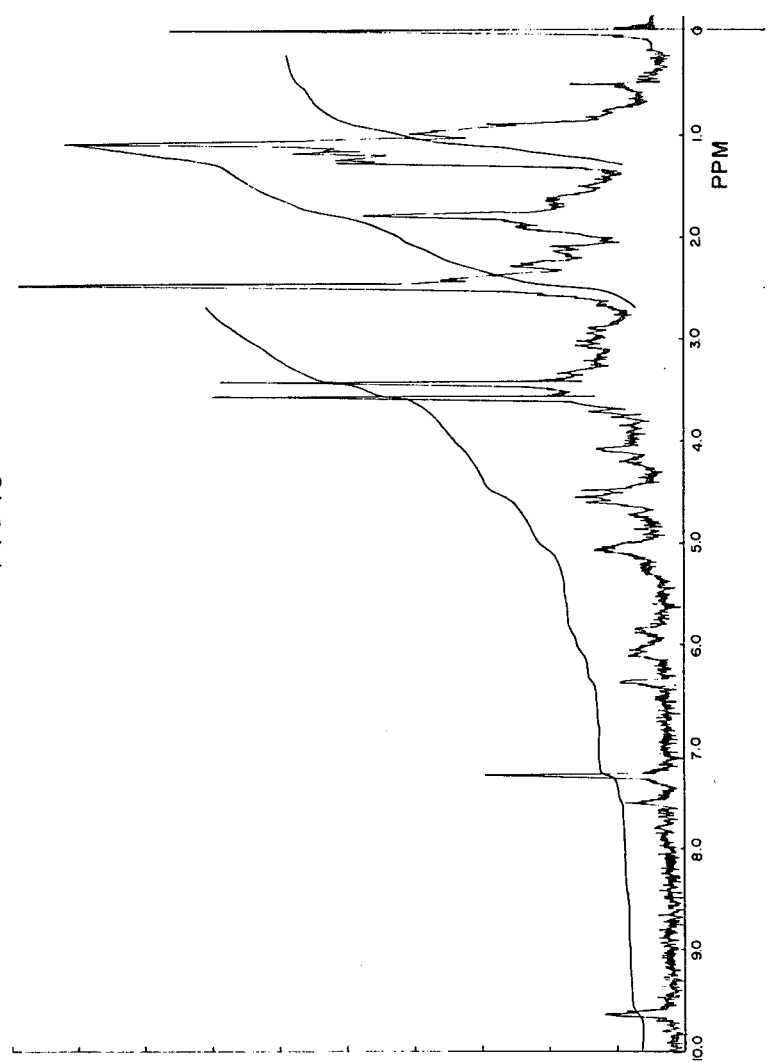
Figure 16:
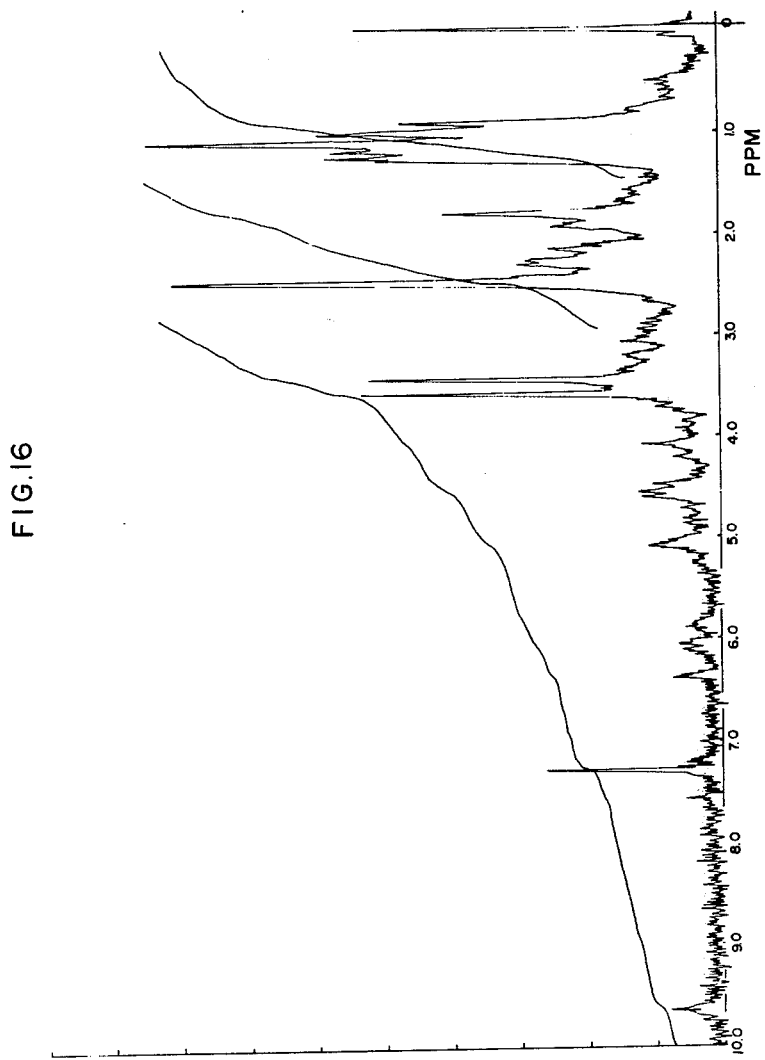
Figure 17:
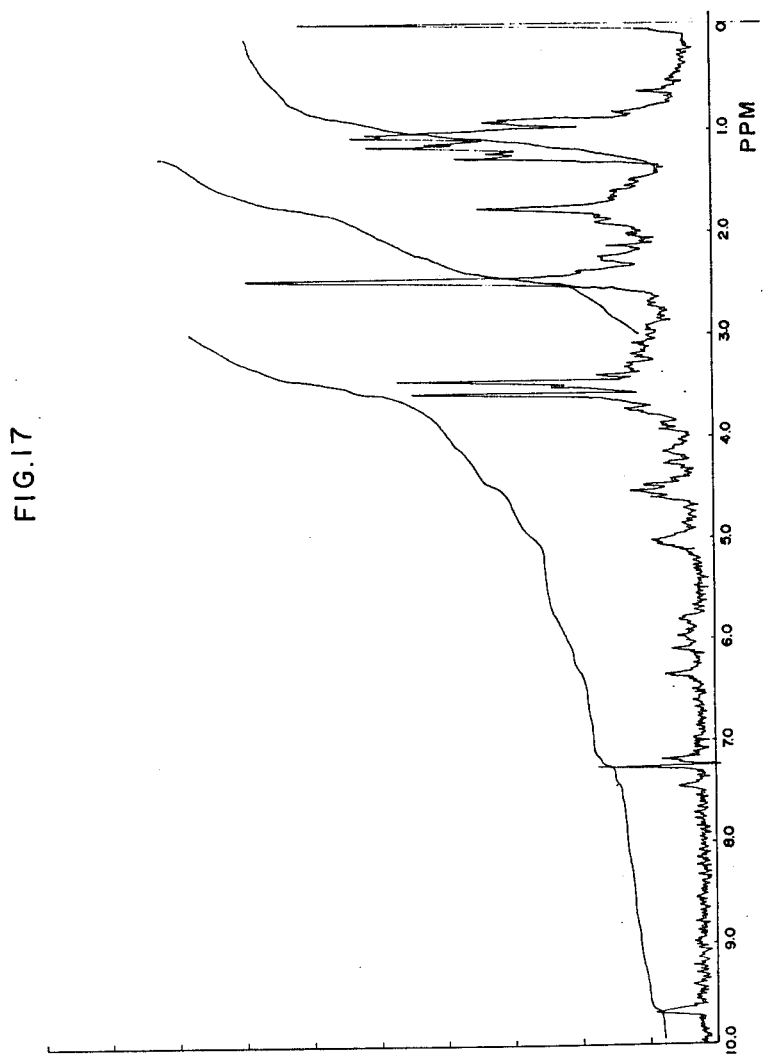
Figure 18:
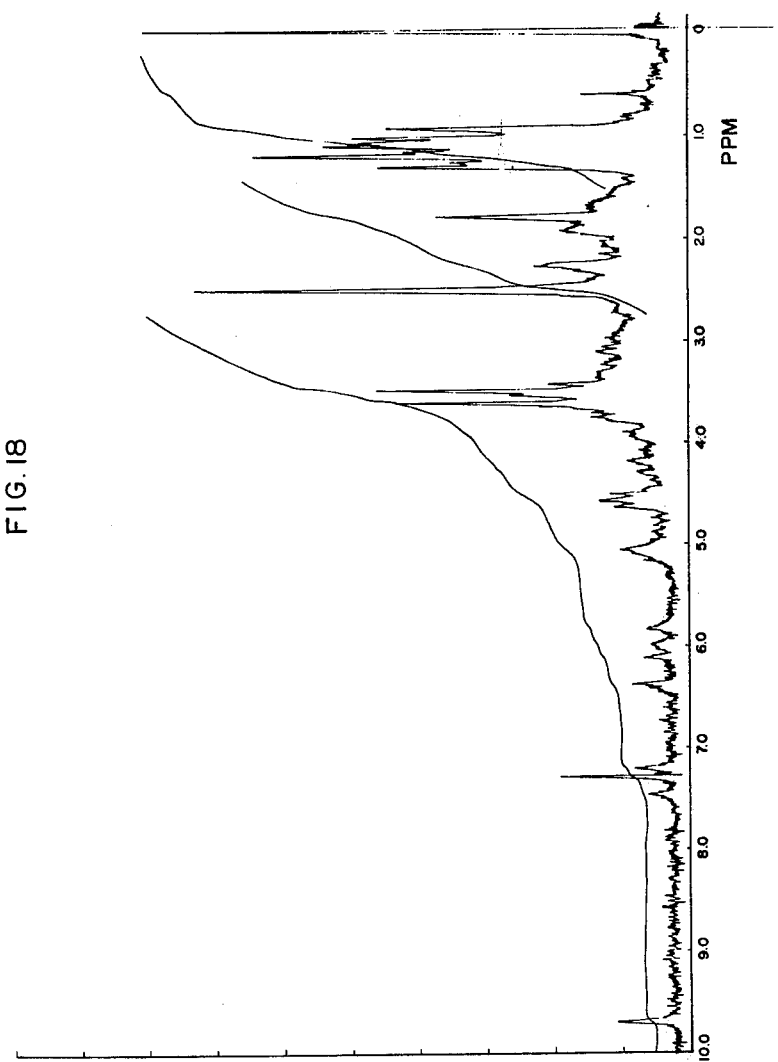
Figure 19:
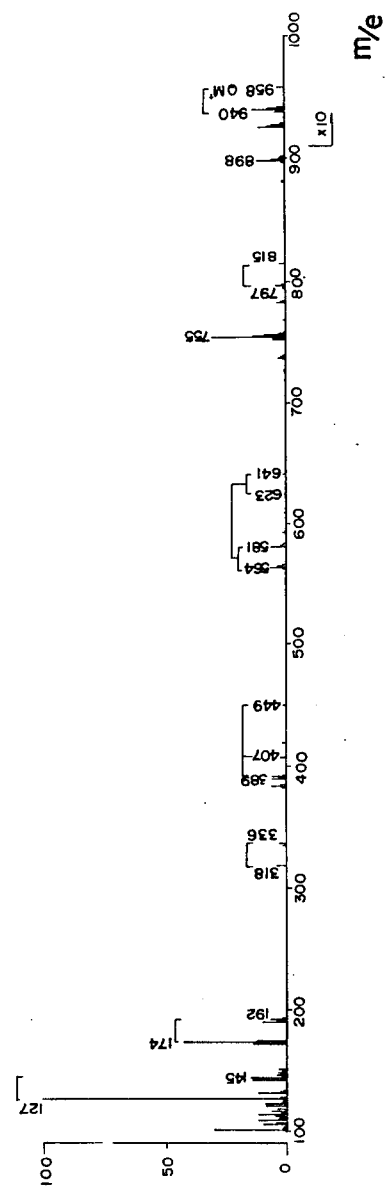
FIGS. 19,20 and 21 are the chemical ionization mass spectra for 3-acetyltylosin, 3-propionyltylosin and 3-acetyl-4"-isovaleryltylosin, respectively.
Figure 20:
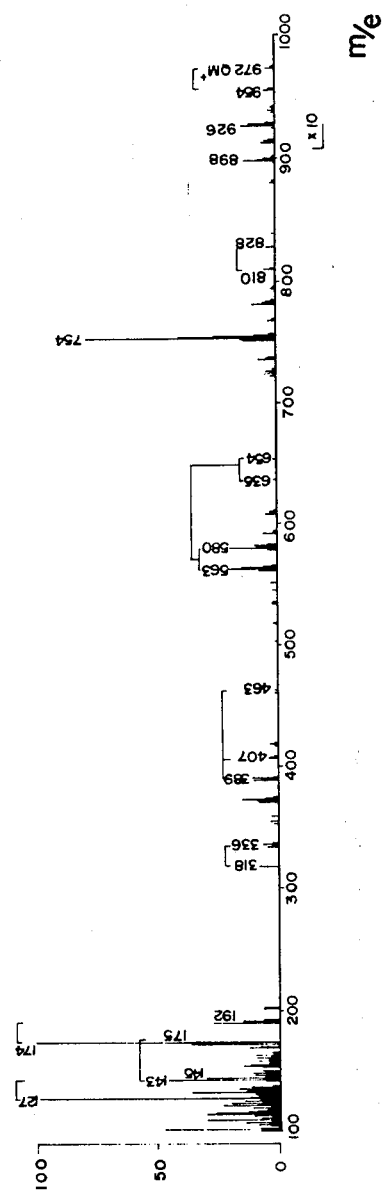
Figure 21:
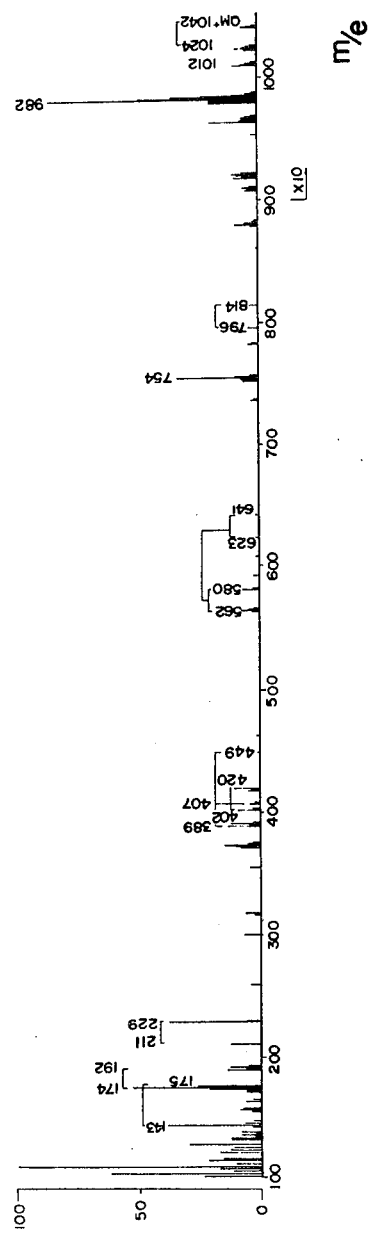

| compound analysis | 3-propionyl-4"-n-butyryltylosin | 3-propionyl-4"-isovaleryltylosin | 4"-n-butyryltylosin | 4"-isovaleryltylosin |
|---|---|---|---|---|
| (7) infrared absorption spectra (KBr pellet) (cm$^{-1}$) | 3435, 2975, 2940, 2885, 2845, 2795, 2730, 1731, 1670, 1626, 1592, 1450, 1404, 1374, 1318, 1270, 1172, 1086, 1055, 1019, 980, 965, 923, 900, 843 | 3490–3440, 2970, 2940, 2885, 2845, 2795, 2710, 1735, 1670, 1627, 1595, 1450, 1412, 1372, 1318, 1300, 1171, 1148, 1122, 1087, 1058, 1025, 1005, 981, 921, 900, 843 | 3490, 2970, 2935, 2880, 2840, 2790, 2715, 1724, 1680, 1625, 1588, 1449, 1406, 1375, 1313, 1266, 1170, 1121, 1083, 1055, 1019, 980, 963, 923, 905, 842, | 3497, 2965, 2935, 2880, 2840, 2790, 2730, 1740, 1730, 1681, 1629, 1639, 1457, 1412, 1454, 1317, 1299, 1279, 1169, 1145, 1121, 1083, 1055, 1028, 1018, 1000, 983, 964, 920, 900 |
| | FIG. 7 | FIG. 8 | FIG. 9 | FIG. 10 |
| (8) NMR (CDCl$_3$) 60MHz | FIG. 15 | FIG. 16 | FIG. 17 | FIG. 18 |
| (9) organic acids detected by gas chromatography | propionic acid and n-butyric acid | propionic acid and isovaleric acid | n-butyric acid | isovaleric acid |

| compound analysis | 3-acetyltylosin | 3-acetyl-4"-n-butyryltylosin | 3-acetyl-4"-isovaleryltylosin | 3-propionyltylosin |
|---|---|---|---|---|
| (10) solubility | soluble in lower alcohols e.g., ethanol ketones, e.g., acetone; ethers e.g., ethyl ether; esters e.g., ethyl acetate; benzene and toluene; hardly soluble in n-hexane and petroleum ether: soluble in acidic water: slightly soluble in neutral water: hardly soluble in alkaline water. | | | |
| (11) color development reaction | Molisch (+), conc-sulfuric acid (+), Ninhydrin (−), Millon (−), Sakaguchi (−) Beuret (−) | | | |
| (12) alkalinity | alkaline compounds | | | |
| (13) solvent used for crystallization | toluene | ethyl ether | ethyl ether | ethyl ether |

| compound analysis | 3-propionyl-4"-n-butyryltylosin | 3-propionyl-4"-isovaleryltylosin | 4"-n-butyryltylosin | 4"-isovaleryltylosin |
|---|---|---|---|---|
| (10) solubilty | soluble in lower alcohols e.g., ethanol ketones, e.g., acetone; ethers e.g., ethyl ether; esters e.g., ethyl acetate; benzene and toluene; hardly soluble in n-hexane and petroleum ether: | | | |

Table 1.-continued

| | Physico-chemical Properties of Tylosin Derivatives | | | |
|---|---|---|---|---|
| | soluble in acidic water: slightly soluble in neutral water: hardly soluble in alkaline water. | | | |
| (11) color development reaction | Molisch (+), conc-sulfuric acid (+), Ninhydrin (−), Millon (−), Sakaguchi (−) Beuret (−) | | | |
| (12) alkalinity | alkaline compounds | | | |
| (13) solvent used for crystallization | ethyl ether | ethyl ether | isopropyl ether-ethyl ether | isopropyl ether ethyl ether |

The ultraviolet spectra shows little difference between the eight compounds as shown in the examples for 4"-n-butyryltylosin (FIG. 1) and 3-acetyl-4"-n-isovaleryltylosin (FIG. 2). The maximum absorption peaks lie between 282-285 nm, which is the same for tylosin, indicating no structural change in the ketone and the double-bond structure of the macrolide ring. By the detection of released organic acid by gas chromatography and from analytical data for molecular weight, the compounds have been shown to have a basic structure in common: tylosin bearing one or two species of acylating groups, i.e., acetyl, propionyl, n-butyryl and isovaleryl residues. In addition, after analysis of the data of IR spectra and NMR spectra, the above-presented structures were confirmed. Data of chemical ionization mass spectrometry are shown for 3-acetyltylosin (FIG. 19, and 3-propionyltylosin (FIG. 20) as examples of 3-acylated derivatives and 3-acetyl-4"-isovaleryltylosin (FIG. 21) as an example of 3- and 4"-acylated ones. Assignments were made for each fragment in the comparison of the data with tylosin, which revealed fragmentation in the $C_5$—O, O—$C_1''$, O—$C_1''$ bonds, dehydration and deacylation in both tylosin and the derivatives. It was thus demonstrated that the acetyl and the propionyl group are bonded to the macrolide ring and that the isovaleryl group is bonded to the mycarose ring. Data for other compounds which are not shown here also gave the same conclusions.

Figure 22:
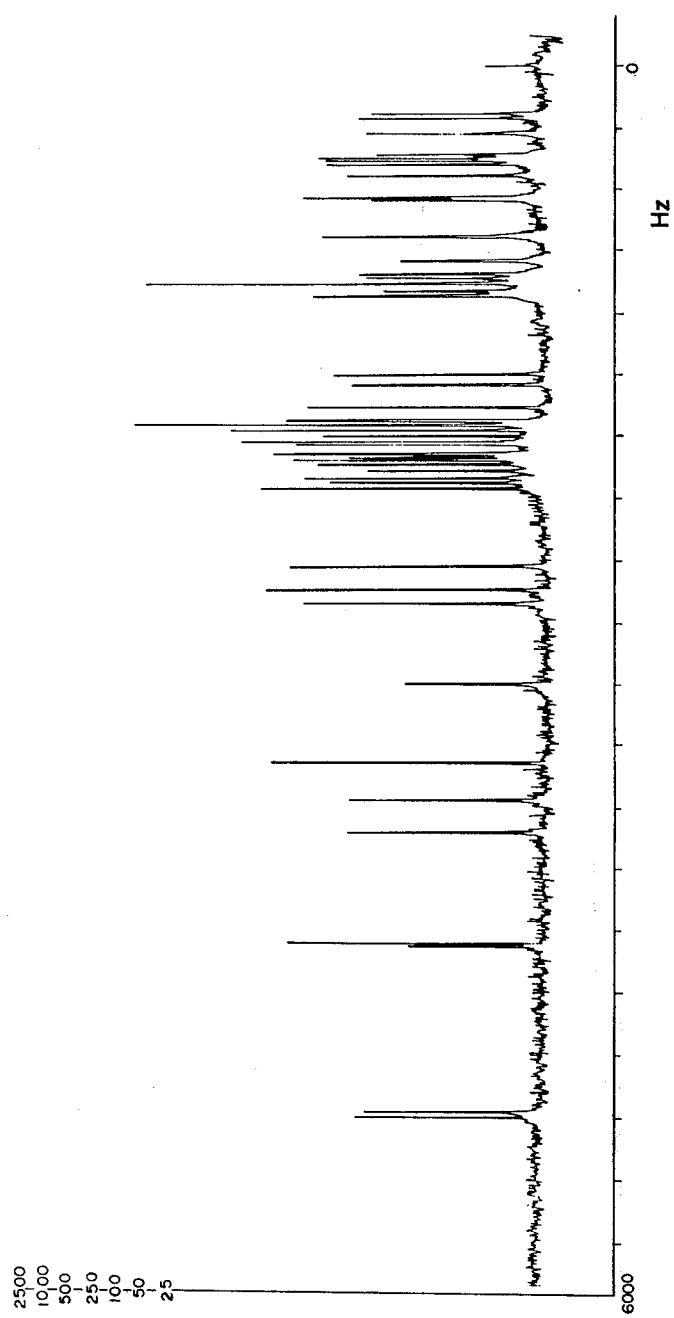
FIGS. 22 and 23 are $C^{13}$-NMR spectra (25.2 MHz) for 3-acetyltylosin and 3-acetyl-4"-isovaleryltylosin
Figure 23:
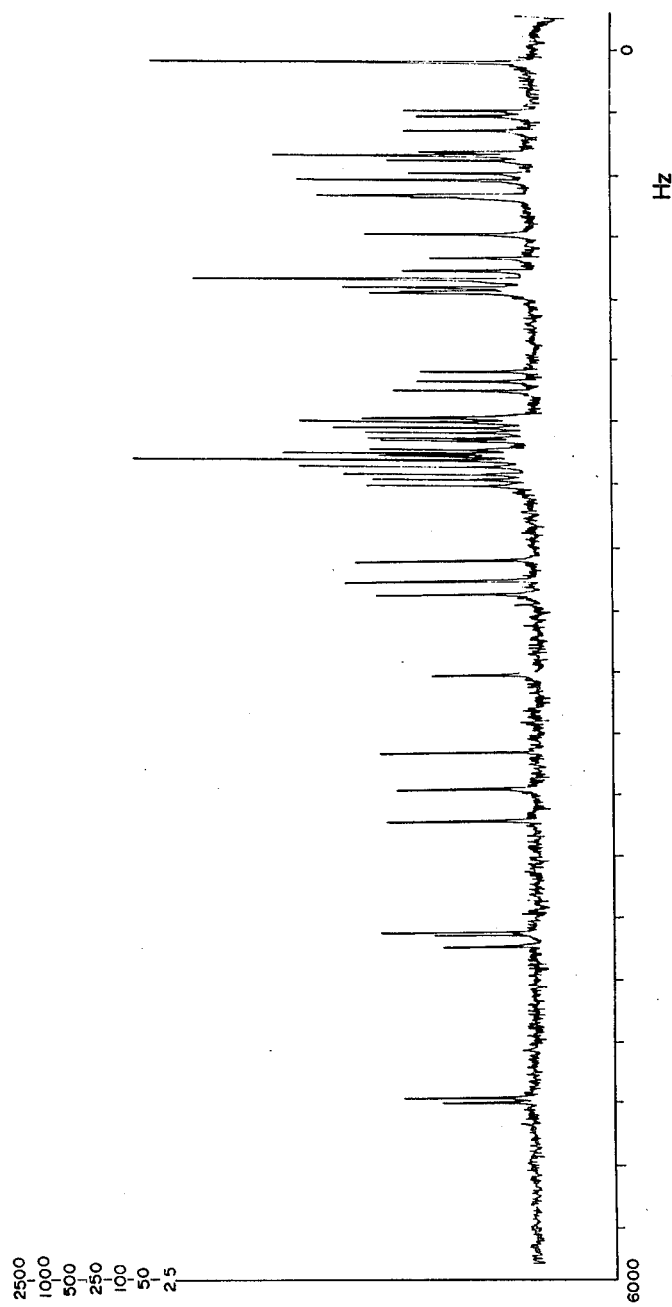

Example of the $C^{13}$ NMR spectra of 3-acetyltylosin for 3-acylated derivatives and with 3-acetyl-4"-isovaleryltylosin for 3- and 4"-acylated derivatives are shown in FIG. 22 and FIG. 23. By results of the assignment of signals, in comparison with that of tylosin, it was further deduced that the acetyl group bonds to the 3-position of the macrolide ring and that the isovaleryl group bonds to the 4"-position of mycarose. Other compounds also have similar data in showing the bonding position for the propionyl group and the n-butyryl group and identified chemical structures.

Further comparisons were undertaken between the derivatives of this invention and those chemically synthesized according to the prior art previously reported. In Japanese Patent (Kokoku) Showa No. 36-22649 entitled "Methods for Producing Tylosin referring to Example 4, the chemical synthesis of tylosin acetyl ester by the use of acetyl chloride is described, and it is noted that the weight content of the acetyl group is 8.22% (by weight) and the pk value is about 5.1 (electrometric determination of the solution in dimethyl formamide—$H_2O$=2:1 by volume).

In Example 5 of the same patent, the synthesis of acetylated tylosin by the use of acetic anhydride as an acetylating agent is also described; the acetyl content being 8.91 (by weight) and the pk value about 5.2. Chemical synthesis of the acetylated tylosin was then performed according to the above methods and a comparison with the corresponding compounds according to the present invention was made for their Rf values on a thin layer chromatogram employing the plate Art 5715 (Merck Co.) and the developmental solvent of ethyl acetate:ethanol:pyridine (85:15:2 by volume).

The 3-acetyltylosin obtained by this invention gave an Rf value of 0.59, while the acetylated tylosin in Example 4 of the aforementioned patent gave 0.71 and the product of Example 5 of the aforementioned patent gave 0.71, 0.75 and 0.83, which is indicative of the mixture of 3 compounds. Other determinations also confirmed differences between the 3-acetyltylosin of this invention and those chemical products. Likewise, in an Example of the aforementioned patent, chemically synthesized propionylated tylosin is shown to have a melting point of 101°–111° C. This value is clearly distinguishable from the value of 187°–192° C. for the 3-propionyltylosin obtained from this invention.

The antimicrobial spectra of new tylosin derivatives of this invention are shown in Table 2 by listing the minimum growth inhibitory concentrations (MIC, mcg/ml). These compounds possess a comparatively broad antibacterial spectrum against gram-positive bacteria. The toxicity of these compounds was tested in animals by intravenous administration, and the $LD_{50}$ values in mice are more than 400 mg/kg with all compounds. In therapeutical experiments with mice manually infected by Staphilococcus aureus SMITH, the $ED_{50}$ values were less than 50 mg/kg (p.o.) with all said tylosin derivatives.

One of the particular advantages of the said tylosin derivatives over known macrolide antibiotics is their distinct antimicrobial activity against drug resistant bacteria. The results of some such tests are included in Table 2.

Table 2.

| | Antimicrobial spectra | | | | | | | | |
|---|---|---|---|---|---|---|---|---|---|
| | minimum growth-inhibitory concentration(mcg/ml) | | | | | | | | |
| test strain | compound 3-acetyl-tylosin | 3-acetyl-4"-n-butyryl-tylosin | 3-acetyl-4"-iso-valeryl-tylosin | 3-propi-onyl-tylosin | 3-propi-onyl-4"-n-butyryl-tylosin | 3-propi-onyl-4"-iso-valeryl-tylosin | 4"-n-butyryl-tylosin | 4"-iso-valeryl-tylosin | tylosin |
| (1) Candida albicans IAM 4905 | >250 | >250 | >250 | >250 | >250 | >250 | >250 | >250 | >250 |

Table 2.-continued

| | Antimicrobial spectra minimum growth-inhibitory concentration(mcg/ml) | | | | | | | | |
|---|---|---|---|---|---|---|---|---|---|
| test strain compound | 3-acetyl-tylosin | 3-acetyl-4″-n-butyryl-tylosin | 3-acetyl-4″-iso-valeryl-tylosin | 3-propi-onyl-tylosin | 3-propi-onyl-4″-n-butyryl tylosin | 3-propi-onyl-4″-iso-valeryl tylosin | 4″-n-butyryl tylosin | 4″-iso-valeryl tylosin | tylosin |
| (2) *Candida tropicalis* IAM 4924 | >250 | >250 | >250 | >250 | >250 | >250 | >250 | >250 | >250 |
| (3) *Pseudomonas fluorescens* NIHJB 254 | >250 | >250 | >250 | >250 | >250 | >250 | >250 | >250 | >250 |
| (4) *Escherichia coli* (National Institute of Health) | 250 | 250 | 125 | 250 | 250 | 250 | 125 | 125 | 250 |
| (5) *Proteus morganii* (The Institute for Infectious Diseases) | >250 | >250 | >250 | >250 | >250 | >250 | >250 | >250 | >250 |
| (6) *Staphylococcus aureus* FAD209P | 0.25 | 0.25 | 0.49 | 0.25 | 0.98 | 0.49 | 0.25 | 0.49 | 0.49 |
| (7) *Staphylococcus aureus* SMITH | 0.12 | 0.25 | 0.49 | 0.12 | 0.25 | 1.95 | 0.25 | 0.25 | 0.25 |
| (8) *Bacillus cereus* ATCC 9634 | 0.49 | 0.98 | 1.95 | 0.25 | 1.95 | 0.98 | 0.98 | 0.98 | 0.49 |
| (9) *Bacillus megaterium* NRRL B-938 | 0.25 | 0.49 | 0.49 | <0.12 | 0.49 | 0.49 | 0.49 | 0.98 | 0.25 |
| (10) *Sarcina lutea* ATCC 9341 | <0.12 | <0.12 | 0.25 | <0.12 | <0.12 | 0.25 | 0.25 | <0.12 | 0.12 |
| (11) *Micrococcus flavus* I | <0.12 | 0.25 | 0.25 | <0.12 | 0.25 | 0.49 | 0.49 | 0.25 | 0.12 |
| (12) *Corynebacterium bovis* 1810 | 0.25 | 0.50 | 0.50 | 0.25 | 0.50 | 1.00 | 0.98 | 0.50 | 0.50 |
| (13) *Mycobacterium smegmatis* ATCC 607 | 7.81 | 1.95 | 3.91 | 3.91 | 3.91 | 3.91 | 3.91 | 3.91 | 7.81 |
| (14) *Bacillus subtilis* ATCC 6633 | 0.49 | 0.49 | 0.98 | 0.25 | 0.49 | 0.49 | 0.49 | 0.49 | 0.49 |
| (15) *Staphylococcus aureus*\*MS 9610 | >250 | 250 | 62.5 | >250 | 250 | 62.5 | >250 | 62.5 | >250 |
| (16) *Staphylococcus aureus*\*MS 8710 | 250 | 15.6 | 15.6 | 62.5 | 31.3 | 15.6 | 62.5 | 15.6 | >250 |
| (17) *Streptococcus pyogenes*\*MH 771 | 125 | 15.6 | 3.91 | 62.5 | 15.6 | 3.91 | 15.6 | 7.80 | 250 |

(broth-dilution method)

Note: *shows drug resistant strain

The strains marked * in Table 2 are the drug resistant strains isolated from patients, namely, *Staphilococcus aureus* MS-9610 which is resistant to penicillin, tetracycline, erythromycin, leucomycin, spiramycin, josamycin and tylosin, *Staphilococcus aureus* MS-8710 which is resistant to penicillin, tetracycline, erythromycin, leucomycin and tylosin, and *Streptococcus pyogenes* MH 771 which is resistant to erythromycin, oleandomycin, leucomycin and tylosin. Among the derivatives of the present invention, those introduced with the 4″-acyl group i.e. 4″-n-butyryltylosin, 4″-isovaleryltylosin, 3-acetyl-4″-n-butyryltylosin, 3-acetyl-4″-isovaleryltylosin, 3-propionyl-4″-n-butryltylosin and 3-propionyl-4″-isovaleryltylosin, exert a particularly strong antimicrobial activity against a wide range of drug resistant strains.

Another phase of advantages of the said tylosin derivatives is their high blood levels in animals. When each of these compounds is orally administered to mice in a dose of 100 mg/kg, their concentrations in blood were measured to be 5-20 mcg/ml, a substantially high value compared to that of tylosin (<1 mcg/ml). In particular, those derivatives having an n-butyryl or isovaleryl residue exhibit excellent absorption through the oral administration route. Their concentrations in blood one hour after administration reached up to 15-20 mcg/ml. These advantages should demonstrate the advanced therapeutical usefulness of these compounds of this invention.

The new tylosin derivatives according to the present invention are basic compounds and form their nontoxic acid addition salts with various organic acids such as tartaric acid, acetic acid, propionic acid, citric acid and succinic acid and inorganic acids such as hydrochloric acid, sulfuric acid and phosphoric acid. These salts are formed, isolated, purified and formulated by the methods generally employed in salt formation for 16-membered macrolide antibiotics. For example, the desired tylosin derivative and the intended acid can be dissolved separately in an appropriate solvent which has a low solubility of salts, e.g., ethyl ether and acetone or their mixture, and then the solution is mixed. The solution is then concentrated, if necessary, and cooled, to yield the crystals of the acid addition salt which are collected and dried to give a white crystalline powder. The resulting salts exhibit a higher solubility in water than the corresponding acylated tylosin derivatives and are preferably used in a therapeutical application.

Examples of such acid addition salts are 3-acetyl-4″-isovaleryltylosin hydrochloride, which has a melting point of 129°-133° C., and 3-acetyl-4″-isovaleryltylosin tartrate, which has a melting point of 119°-122° C.

Because of their particular antimicrobial activity, the compounds of this invention are useful as infection-controlling agents in human and veterinary medicine, and can be employed, for example, in the enteral, parenteral or topical control of infectious diseases in a similar manner as for known macrolide antibiotic drugs.

In addition, due to the particular usefulness of tylosin as an animal growth-promoting agent, the said compounds of this invention can also be employed as a feed-additive for use in animal breeding.

The compounds of this invention can be employed in mixtures with conventional excipients and carriers, i.e., pharmaceutically-acceptable organic or inorganic carrier substances suitable for enteral, parenteral or topical application which do not deleteriously react with the active compounds.

Suitable, pharmaceutically acceptable carriers, include but are not limited to water, salt solutions, alcohols, vegetable oils, polyethylene glycols, gelatin, lactose, amylose, magnesium stearate, talc, silicic acid, paraffins, perfume oil, fatty acid monoglycerides and diglycerides and hydroxy methylcellulose. The pharmaceutical preparations can be sterilized and, if desired, mixed with auxiliary agents, e.g., lubricants, preservatives, stabilizers, wetting agents, emulsifiers, buffers, coloring or flavoring substances which do not deleteriously react with the active compounds.

The compounds of this invention can also be employed in feed additive forms such as feed premix in conventional formulation methods.

For animals, including humans, livestock, household pets, laboratory animals and poultry, enteral and intramuscular administration is preferred, for example, in the form of tablets, dragees, capsules, syrups and elixirs, in the form of injection solutions or in the form of feed-additive mixtures. An effective daily dosage of the compounds, as administered orally to humans, comprises preferably 1 to 20 mg per kg of body weight. The dose can be administered singly or in divided dosages throughout the day.

Without further elaboration, it is believed that one skilled in the art can, using the preceeding description, utilize the present invention to its fullest extent. The following preferred specific embodiments are, therefore, to be construed as merely illustrative and not limitative of the remainder of the disclosure in any way whatsoever.

EXAMPLE 1

The production of 4"-butyryltylosin from tylosin

An aqueous medium of the following composition was prepared: soybean flour 2 g/dl, glucose 2 g/dl, yeast extract 0.1 g/dl, $K_2HPO_4$ 0.05 g/dl and $MgSO_4.7H_2O$ 0.05 g/dl. (pH 7.0). 100 ml of this medium was sterilized at 120° C. for 20 min. in a 500 ml-volume Erlenmyer flask and then was inoculated from an agar slant culture of *Streptomyces thermotolerans* ATCC 11416 by a platinum loop. Cultivation proceeded for one day at 37° C. on a rotary shaker. Fifteen liters of the medium supplemented with an antifoam agent, in a concentration of 0.05 g/dl and sterilized at 120° C. for 15 min. in a 30 liter jar fermenter, were aseptically inoculated with 100 ml of the above seed culture. Cultivation was carried out at 37° C. under vigorous agitation and aeration for about one day until the concentration of glucose in the broth decreased to below 0.3 g/dl, at which time 60 g of tylosin and 15 g of DL-norvaline, as a donor of the n-butyryl group were suspended together in a liter of water and were added to the mixture. The reaction was continued for about 6 more hours to complete the conversion reaction.

The reaction mixture thus obtained was adjusted to a pH of 3.5 with dilute sulfuric acid and separated from the mycelia by centrifugation to yield about 16 liters including the rinse of supernatant liquid. The supernatant was adjusted to a pH of 6.0 with dilute sodium hydroxide solution and extracted at 30° C. with 10 liters of benzene. The benzene layer containing the 4"-n-butyryltylosin was separated and extracted at 5° C. with 2 liters of citrate buffer solution of a pH of 3.5. The recovered aqueous layer, after being adjusted to a pH of 7.0 with dilute sodium hydroxide solution, was added to one liter of ethyl acetate for extraction, and the solvent extract was concentrated and dried up in vacuo to yield about 5 g of a yellowish brown material containing the 4"-n-butyryltylosin. This material was charged onto a column 60 cm in length and 2.1 cm in diameter, filled with Wakogel C-200(Trade name of Wako Reagent Chemical Co.), and eluted with a benzene:methanol (97:3) mixture. The eluates, which contain only 4"-n-butyryltylosin, were collected and concentrated to the point of dryness in vacuo. This material was then dissolved in a heated ethyl ether and isopropyl ether (4:1) mixture, and the solution was left standing to allow the ethyl ether to evaporate gradually to allow crystal formation. About 1.5 g of white crystals of the 4"-n-butyryltylosin were obtained.

On the other hand, after extraction with benzene the aqueous layer was adjusted to a pH of 8.0, and extracted with 15 liters of ethyl acetate at 30° C. This extract was mixed with 15 liters of citrate buffer solution of a pH of 3.5 at 5° C., and the recovered aqueous layer was adjusted to a pH of 8.0 with a dilute sodium hydroxide solution and extracted with 10 liters of benzene at 30° C. The extract was concentrated to a volume of 150 ml under reduced pressure, and was left standing at 7° C. to yield crystals of 3-acetyltylosin. After being collected by filtration and then dried, 25 g of white crystals were obtained.

(m.p.: 4"-n-butyryltylosin 149° C., 3-acetyltylosin 216° C.)

EXAMPLE 2

The production of 4"-isovaleryltylosin from tylosin

A similar cultivation and reaction as in Example 1 was carried out by substituting L-leucine as the isovaleryl donor for DL-norvaline. From 60 g of tylosin and 15 g of L-leucine, about 900 mg of white crystals of 4"-isovaleryltylosin and 17 g of white crystals of 3-acetyltylosin were obtained.

(m.p.: 4"-isovaleryltylosin 155° C., 3-acetyltylosin 218° C.)

EXAMPLE 3

The production of 3-acetyltylosin from tylosin

A similar cultivation as in Example 1 was carried out with the same strain in which a culture medium of the following composition was employed; 4 g/dl of soybean flour, 5 g/dl of glucose, 0.02 g/dl of $K_2HPO_4$, 0.05 g/dl of $MgSO_4.7H_2O$ and 0.05 g/dl of an antifoam agent.

After microbial growth for about one day, at which time the concentration of glucose decreased to about 2 g/dl, 30 g of tylosin tartrate in 500 ml of an aqueous solution was added to the cultivated broth and the reaction was continued for a further 8 hours.

After a pH adjustment to 3.5 with dilute sulfuric acid the reaction mixture was treated by centrifugation. The resulting supernatant was adjusted to a pH of 8.0 with dilute sodium hydroxide and extracted twice with 5 liters of ethyl acetate at 30° C. The combined ethyl acetate extract (about 9 liters) was added to 10 liters of citrate buffer solution of a pH of 3.5 at 5° C., and the aqueous layer was separated. After adjusting the pH to 8.0 with a dilute sodium hydroxide solution, this layer was extracted twice each with 5 liters of benzene at 30° C., and the extract was concentrated under reduced pressure to a volume of 100 ml. The concentrate was left standing at 7° C. for 2 days, resulting in the formation of crystals which were collected and dried. About 16 g of white crystals of 3-acetyltylosin was obtained. (m.p.: 3-acetyltylosin 218° C.)

EXAMPLE 4

The production of 3-acetyl-4"-n-butyryltylosin from tylosin

A similar cultivation was made with the same strain, medium and culture conditions as in Example 1. When glucose was consumed to a concentration of about 0.5 g/dl, 3 g of tylosin and 15 g of DL-norvaline in powdered form were added to about 15 liters of broth in a jar fermenter. After 8 hours reaction the reaction mixture recovered was adjusted to a pH of 3.5 with dilute sulfuric acid. After centrifuging the cell mass, the supernatant was adjusted to a pH of 8.0 with dilute sodium hydroxide solution, and extracted with 4 liters of ethyl acetate twice at 30° C. The extract of about 7.5 liters of ethyl acetate layer was concentrated with 1 liter in vacuo, to which was mixed 500 ml of a citrate buffer solution of a pH of 3.5 at 5° C. for the extraction of the formed tylosin derivatives into an aqueous layer. This extraction was repeated, and the combined aqueous layer was adjusted to a pH of 8.0 with a dilute sodium hydroxide solution and extracted twice each time with 300 ml of ethyl acetate at 30° C. This extract was concentrated to the point of dryness, yielding a yellowish brown powder. This powder was applied on a column filled with Wakogel C-200 of 2.1 cm in a diameter and 60 cm in length and elution was carried out with a mixture of benzenemethanol (97:3) in order to collect the fractions containing 3-acetyl-4"-n-butyryltylosin. After evaporation of the solvent, the residue was dissolved in a small amount of ethyl ether by warming, and, then, by cooling, crystals were obtained which were collected and dried for the recovery of 530 mg of crystals of 3-acetyl-4"-n-butyryltylosin.
(m.p.: 3-acetyl-4"-n-butyryltylosin 178° C.)

EXAMPLE 5

The production of 3-acetyl-4"-n-butyryltylosin from 3-acetyltylosin

In a manner similar to Example 4 with the same strain, in which tylosin was substituted as the substrate by 1.5 g of acetyltylosin, 530 mg of white crystals of 3-acetyl-4"-n-butyryltylosin were obtained.
(m.p.: 3-acetyl-4"-n-butyryltylosin 180° C.)

EXAMPLE 6

The production of 3-acetyl-4"-n-butyryltylosin from 4"-n-butyryltylosin

The conversion reaction was carried out with the same strain in a manner similar to Example 3 (3-acetylation), in which 4"-n-butyryltylosin was used as the substrate in an amount of 500 mg. The products were isolated and purified by substantially the same methods as in Example 4. About 250 mg of white crystals of 3-acetyl-4"-n-butyryltylosin were obtained.
(m.p.: 3-acetyl-4"-n-butyryltylosin 177° C.)

EXAMPLE 7

The production of 3-acetyl-4"-isovaleryltylosin from tylosin

The conversion reaction was carried out in a manner similar to Example 4 with the same strain, in which L-leucine was used in substitution for DL-norvaline in Example 4 as the isovaleryl donor. About 400 mg of white crystals of 3-acetyl-4"-isovaleryltylosin were obtained from 3 g of tylosin.
(m.p.: 3-acetyl-4"-isovaleryltylosin 180° C.)

EXAMPLE 8

The production of 3-acetyl-4"-isovaleryltylosin from 3-acetyltylosin

The conversion reaction was carried out in a manner similar to Example 7 with the same strain, in which 1.5 g of 3-acetyltylosin were used as the substrate in place of tylosin. About 500 mg of white crystals of 3-acetyl-4"-isovaleryltylosin were obtained.
(m.p.: 3-acetyl-4"-isovaleryltylosin 184° C.)

EXAMPLE 9

The production of 3-acetyl-4"-isovaleryltylosin from 4"-isovaleryltylosin

Cultivation and reaction were carried out in a manner similar to Example 3 with the same strain, using 500 mg of 4"-isovaleryltylosin as the substrate, and the product was recovered in a manner similar to Example 4. 280 mg of white crystals of 3-acetyl-4"-isovaleryltylosin were obtained.
(m.p.: 3-acetyl-4"-isovaleryltylosin 182° C.)

EXAMPLE 10

The production of 3-propionyltylosin from tylosin

A similar cultivation as in Example 1 was conducted with the same strain, the same seed medium and the same conditions for cultivation. 15 liters of a main medium consisting of 3 g/dl of peptone, 1 g/dl of glucose, 1 g/dl of starch, 0.2 g/dl of $K_2HPO_4$, 0.1 g/dl of $MgSO_4.7H_2O$ and 0.05 g/dl of antifoam agent(pH 7.0) was sterilized at 120° C. for 15 minutes in a far fermenter (total volume 30 liters) and cooled. 100 ml of seed culture was inoculated into the main medium and cultivation was carried out for 18 hours until the added glucose was almost used up and the pH came to 7.5, and then 3 g of tylosin and 30 g of α-amino butyric acid were added to the broth to further the reaction for another 6 hours under the same conditions as the cultivation. The reaction mixture was taken from the jar fermenter, and the product was isolated and recovered according to the methods employed in Example 4 to obtain about 850 mg of white crystals of 3-propionyltylosin.
(m.p.: 3-propionyltylosin 189° C.)

EXAMPLE 11

The production of 3-propionyl-4"-n-butyryltylosin from tylosin

A similar cultivation was conducted with the same strain, the same seed and main medium and the same conditions for cultivation as in Example 10. Cultivation was carried out until the added glucose was completely consumed and the pH came to 7.5, and then 1.5 g of tylosin and 30 g of α-amino butyric acid as a propionyl group donor were added to the broth(15 liters) in order to carry out the propionylation of a hydroxy group at the 3-position under the same conditions as for cultivation.

When propionylation was completed, 4 hours after the addition of tylosin and α-amino butyric acid, 30 g of DL-norvaline as a precursor of n-butyryl group donor, was added and the reaction was further carried out under the same conditions described above, for 6 more hours, by which a hydroxy group at 4"-position was n-butyrylated. The product was isolated from the reaction mixture and recovered according to methods employed in Example 4 to obtain about 220 mg of white crystals of 3-propionyl-4"-n-butyryltylosin.
(m.p.: 3-propionyl-4"-n-butyryltylosin 185° C.)

EXAMPLE 12

The production of 3-propionyl-4"-n-butyryltylosin from 3-propionyltylosin

Methods similar to those in Example 11 were conducted with the same strain by substituting 500 mg of 3-propionyltylosin as the substrate for tylosin and α- amino butyric acid with the omission of the propionylation of a hydroxy group at 3-position and then a hydroxy group at 4"-position was n-butyrylated to obtain 180 mg of white crystals of 3-propionyl-4"-n-butyryltylosin.
(m.p.: 3-propionyl-4"-n-butyryltylosin 183° C.)

EXAMPLE 13

The production of 3-propionyl-4"-n-butyryltylosin from 4"-n-butyryltylosin 500 mg of 4"-n-butyryltylosin was used as a substrate. A hydroxy group at 3-position was propionylated according to the methods employed in Example 10, and the product was isolated and recovered according to the methods employed in Example 4 to obtain about 370 mg of white crystals of 3-propionyl-4"-n-butyryltylosin.
(m.p.: 3-propionyl-4"-n-butyryltylosin 185° C.)

EXAMPLE 14

The production of 3-propionyl-4"-isovaleryltylosin from tylosin

Methods similar to those employed in Example 11 were used with the same strain by substituting L-leucine as a precursor of the isovaleryl group for DL-norvaline as a precursor of n-butyryl group and a hydroxy group at 4"-position was isovalerylated, and 80 mg of white crystals of 3-propionyl-4"-isovaleryltylosin were obtained from 1.5 g of tylosin.
(m.p.: 3-propionyl-4"-isovaleryltylosin 181° C.)

EXAMPLE 15

The production of 3-propionyl-4"-isovaleryltylosin from 3-propionyltylosin

A cultivation similar to that of Example 10 was conducted with the same strain, the same medium and the same conditions for cultivation.

Cultivation was carried out until the concentration of glucose in the medium decreased to lower than 0.5 g/dl, and then 1 g of 3-propionyltylosin and 20 g of L-leucine were added to the broth (about 15 liters) to carry out the reaction for 6 hours under the same conditions as cultivation. The product was isolated and recovered according to the methods employed in Example 4 to obtain 20 mg of white crystals of 3-propionyl-4"-isovaleryltylosin
(m.p.: 3-propionyl-4"-isovaleryltylosin 185° C.)

EXAMPLE 16

The production of 3-propionyl-4"-isovaleryltylosin from 4"-isovaleryltylosin 500 mg of 4"-isovaleryltylosin were used as a substrate and a hydroxy group at 3-position was propionylated according to the methods employed in Example 10. The product was isolated and recovered according to the methods employed in Example 4 to obtain about 85 mg of white crystals of 3-propionyl-4"-isovaleryltylosin.
(m.p.: 3-acetyl-4"-isovaleryltylosin 183° C.)

Figure 24:
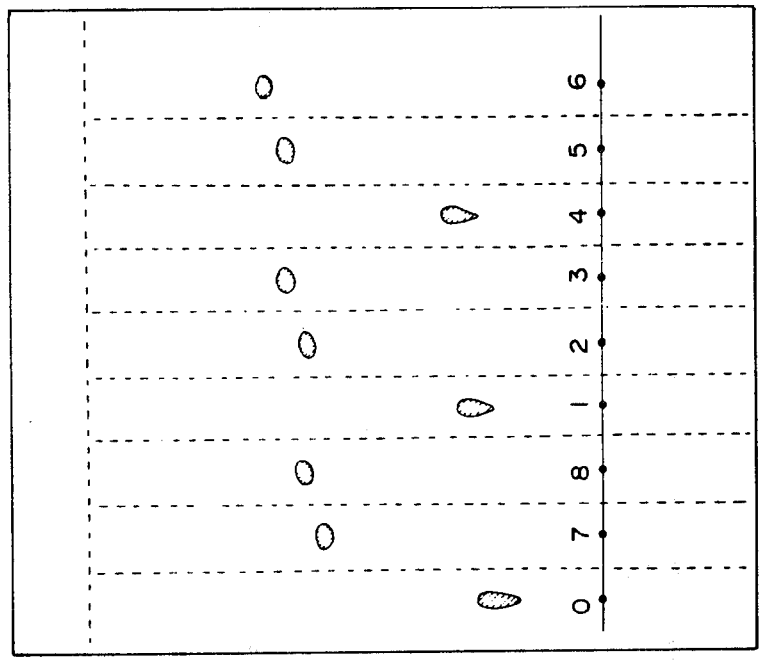
FIG. 24 is a thin layer chromatogram of the tylosin derivatives of this invention.
Figure 24:
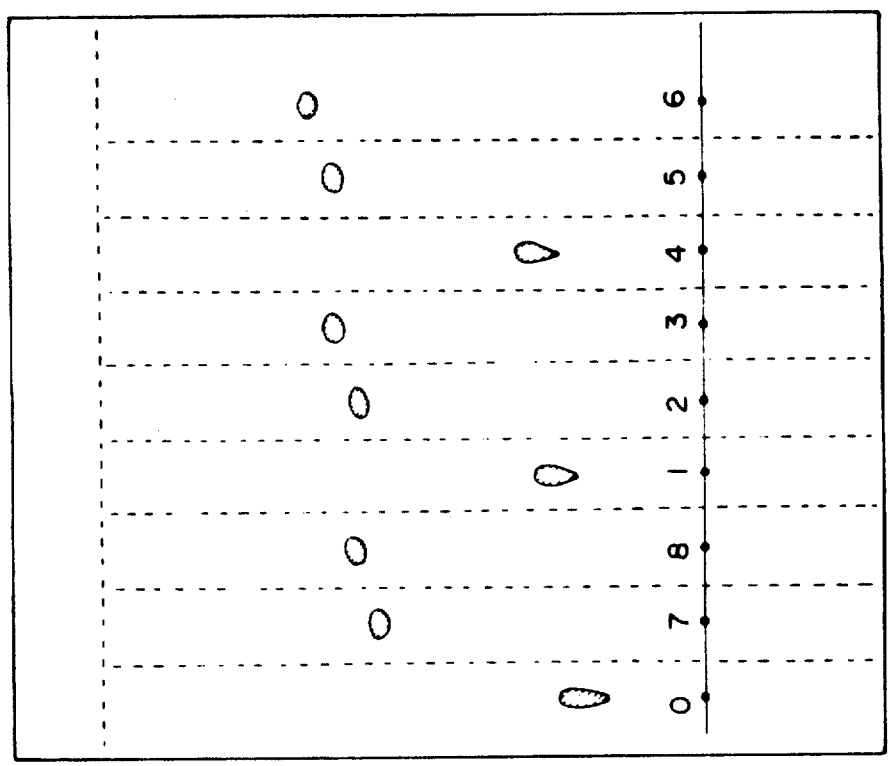

The derivatives of tylosin obtained in Examples 1–16 were respectively analyzed and the structures identified by UV spectrum, IR spectrum, NMR spectrum, mass spectrum(chemical ionization), melting point, specific rotation, elementary analysis, gas chromatography of organic acid released by alkaline hydrolysis, etc., and, if necessary, the compounds were compared to and identified respectively by mixed melting point determination and thin layer chromatography as in FIG. 24, wherein numbers 0, 1 and 8 are the spots of tylosin and the tylosin derivatives in the order of those which appear in Table 1.

EXAMPLE 17

Similar cultivation and reaction was conducted as in Example 1. 100 ml of each medium was placed in respective, sterilized 16 500 ml volume flasks, and cultivation was carried out for 2 days in the same manner as for the seed culture in Example 1 until added glucose was completely consumed. 100 mcg/ml of tylosin or derivatives thereof was added as the substrates to each of the flasks, and then each of 0.1 g/dl of the materials shown in Table 3 were added as the precursors of the acyl group, and the reaction was carried out for 12 hours under the same conditions as for cultivation. The reaction mixtures were adjusted to weakly alkaline and the products were extracted with benzene to be analyzed by thin layer chromatography. The products were identified by their comparison to the authentic derivatives of tylosin, employing parallel development and double spotting development techniques. The interrelation between substrate, acyl precursors and products are shown in Table 3.

Table 3

| Interrelation between substrates, acyl precursors and products | | |
|---|---|---|
| substrates | acyl precursors | products |
| tylosin | α-keto butyric acid | 3-propionyltylosin |
| tylosin | sodium propionate | 3-propionyltylosin |
| 4"-n-butyryltylosin | α-keto butyric acid | 3-propionyl-4"-n-butyryltylosin |
| 4"-n-butyryltylosin | sodium propionate | 3-propionyl-4"-n-butyryltylosin |
| 4"-isovaleryltylosin | α-keto butyric acid | 3-propionyl-4"-isovaleryltylosin |
| 4"-isovaleryltylosin | sodium propionate | 3-propionyl-4"-isovaleryltylosin |
| 3-acetyltylosin | α-keto-n-valeric acid | 3-acetyl-4"-n-butyryltylosin |
| 3-acetyltylosin | n-butyric acid | 3-acetyl-4"-n-butyryltylosin |
| 3-acetyltylosin | ethyl n-butylate | 3-acetyl-4"-n-butyryltylosin |
| 3-acetyltylosin | n-butyryl amide | 3-acetyl-4"-n-butyryltylosin |
| tylosin | isovaleric acid | 4"-isovaleryltylosin |
| tylosin | ethyl isovalerate | 4"-isovaleryltylosin |
| tylosin | isovaleryl amide | 4"-isovaleryltylosin |
| 3-acetyltylosin | isovaleric acid | 3-acetyl-4"-isovaleryltylosin |
| 3-acetyltylosin | ethyl isovalerate | 3-acetyl-4"-isovaleryltylosin |
| 3-acetyltylosin | isovaleryl amide | 3-acetyl-4"-isovaleryltylosin |

EXAMPLE 18

The microorganisms, *Streptomyces thermotolerans* ATCC 11416, *Streptomyces fungicidicus* subsp. *espinomyceticus* ATCC 21574, *Streptomyces hygroscopicus* ATCC 21582 and *Streptomyces mycarofaciens* ATCC 21454, respectively, were employed and the cultivation and the reaction was carried out as follows;

The same in a medium similar to that in Example 17 was employed. *Streptomyces thermotolerans* ATCC 11416 was cultivated at 37° C. and other strains were cultivated at 28° C. on a rotary shaker. After 30 hours, 300 ml of the broth (3 flasks) was filtered to collect living cells, which was suspended in Tris-HCl buffer solution(pH 7.2, M/10) and the cells were broken by a French-press. Each 3 ml of said buffer solution containing broken cells was placed in L-type test tube fermenters. To each fermenter was added 40 mcg/ml of tylosin or derivatives thereof as substrates and then were added various kinds of acyl CoA listed in Table 4 in equivalent molar concentrations. The fermenters were shaken slowly during one hour's reaction. The reaction was terminated by adding glycine-NaOH buffer solution. The products were extracted with benzene and identified in the same manner as described above. Similar results were obtained with those microorganisms described above.

The interrelation among substrates, acyl CoA and the products is shown in Table 4.

Table 4

Interrelation among substrates, acyl CoA and products

| substrates | acyl CoA | products |
|---|---|---|
| tylosin | acetyl CoA | 3-acetyltylosin |
| tylosin | propionyl CoA | mainly 3-propionyltylosin |
| tylosin | n-butyryl CoA | mainly 4''-n-butyryltylosin |
| tylosin | isovaleryl CoA | 4''-isovaleryltylosin |
| 3-acetyltylosin | acetyl CoA | no reaction |
| 3-acetyltylosin | n-butyryl CoA | 3-acetyl-4''-n-butyryltylosin |
| 3-acetyltylosin | isovaleryl CoA | 3-acetyl-4''-isovaleryltylosin |
| 3-propionyltylosin | n-butyryl CoA | 3-propionyl-4''-n-butyryltylosin |
| 3-propionyltylosin | isovaleryl CoA | 3-propionyl-4''-isovaleryltylosin |
| 4''-n-butyrytylosin | acetyl CoA | 3-acetyl-4''-n-butyryltylosin |
| 4''-n-butyryltylosin | propionyl CoA | 3-propionyl-4''-n-butyryltylosin |
| 4''-isovaleryltylosin | acetyl CoA | 3-acetyl-4''-isovaleryltylosin |
| 4''-isovaleryltylosin | propionyl CoA | 3-propionyl-4''-isovaleryltylosin |

EXAMPLE 19

The production of 3-acetyl-4''-isovaleryltylosin tartrate 1 g of 3-acetyl-4''-isovaleryltylosin was dissolved in 40 ml of acetone, and 0.11 g of tartaric acid was dissolved in 20 ml of acetone. Both solutions were mixed, concentrated to 40 ml and maintained at 5° C. for one day.

The crystals from the combined solution were collected by filtration and dried to yield 0.9 g of white crystals of 3-acetyl-4''-isovaleryltylosin tartrate. (Melting point 119° C.–122° C.)

EXAMPLE 20

The production of 3-acetyl-4''-isovaleryltylosin hydrochloride 1 g of 3-acetyl-4''-isovaleryltylosin was dissolved in 120 ml of ethyl ether and 0.08 ml of concentrated hydrochloric acid was dissolved in 30 ml of a mixture of ethyl ether and acetone. Both solutions were mixed and cooled in ice and maintained at 5° C. for one day. Crystals from the mixed solution were collected by filtration and dried to yield 0.8 g of white crystals of 3-acetyl-4''-isovaleryltylosin hydrochloride. (Melting point 129° C.–133° C.)

EXAMPLE 21

Two kinds of tablets (A and B) suitable for oral administration and containing the following ingredients were prepared by conventional tabletting techniques.

| Ingredient: | | Weight (mg.) |
|---|---|---|
| (A) | 3-acetyl-4''-isovaleryltylosin | 200 |
| | Sodium carboxymethylcellulose | 8 |
| | Lactose | 172 |
| | Corn starch | 20 |
| | Magnesium stearate | 2 |
| (B) | 3-propionyl-4''-n-butyrytylosin | 100 |
| | Tragacanth | 4 |
| | Lactose | 82.5 |
| | Corn starch | 10 |
| | Talcum | 2 |
| | Magnesium stearate | 1.5 |

EXAMPLE 22

Dry filled capsules suitable for oral administration, containing the following ingredients were prepared in the conventional manner.

| Ingredient: | Weight (mg.) |
|---|---|
| 3-acetyl-4''-n-butryltylosin | 200 |
| Inert solid diluent(e.g., Starch, Lactose) | 198 |
| Magnesium stearate | 2 |

The tablets or capsules so prepared are administered to a patient at a dose of 2 to 4 tablets or capsules a day.

The proceeding examples can be repeated with similar success by substituting the generically or specifically described reactants and operating conditions of this invention for those used in the preceeding examples.

What is claimed is:

1. A process for producing acyl derivatives of tylosin having the general formula I,

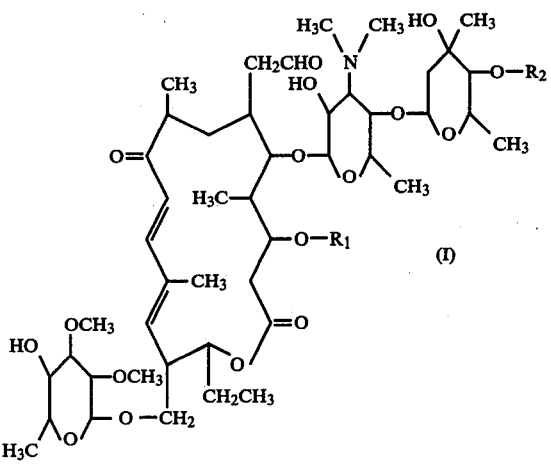

wherein
R$_1$ is H, acetyl or propionyl group and R$_2$ is H, n-butyryl or isovaleryl group, the case where both R$_1$ and R$_2$ are H being excluded, and
the acid addition salts thereof, from a tylosin substrate having the general formula I',

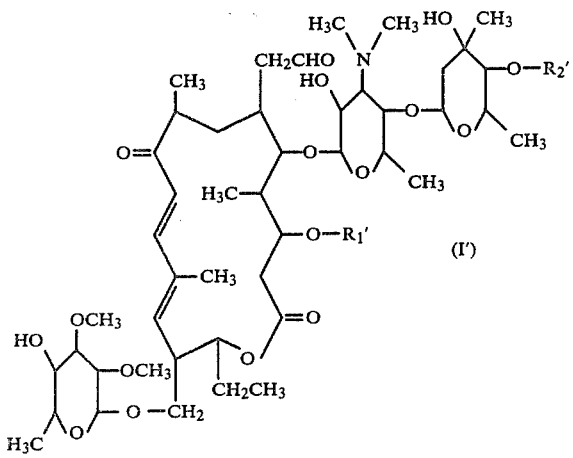

wherein
both $R_1'$ and $R_2'$ are H, or one of them is H and the other is $C_2$–$C_5$ acyl group, which comprises incubating said tylosin substrate with a microbial agent obtained from a microorganism belonging to the genus Streptomyces and capable of acylating at least one hydroxyl group at the 3- and 4″-positions of said substrate in the presence of $C_2$–$C_5$ acyl donor, said microbial agent being selected from a growing cell in a culture medium, a resting cell, a dried cell, a cell homogenate of said microorganism, a supernatant solution and an enzymatic preparation obtained therefrom.

2. A process, as claimed in claim 1, for producing acyl derivatives of tylosin and the acid addition salts thereof wherein the hydroxyl group at the 3-position of tylosin or the 3-position of acyl derivatives of tylosin, in which $R_2'$ at the 4″-position is hydrogen or acyl group, as shown in formula I′, is acylated.

3. A process, as claimed in claim 2, for producing an acyl derivative of tylosin and the acid addition salts thereof wherein the acylation of the hydroxyl group at the 3-position of tylosin, shown in formula I′ is acetylation.

4. A process, as claimed in claim 2, for producing an acyl derivative of tylosin and the acid addition salts thereof wherein the acylation of the hydroxyl group at the 3-position of the derivative of tylosin, in which $R_2'$ at the 4″-position is n-butyryl group, as shown in formula I′ is acetylation.

5. A process, as claimed in claim 2, for producing an acyl derivative of tylosin and the acid addition salts thereof wherein the acylation of the hydroxyl group at the 3-position of the derivative of tylosin in which $R_2'$ at the 4″-position is isovaleryl group, as shown in formula I′ is acetylation.

6. A process, as claimed in claim 2, for producing an acyl derivative of tylosin and the acid addition salts thereof wherein the acylation of the hydroxyl group at the 3-position of tylosin, as shown in formula I′, is propionylation.

7. A process, as claimed in claim 2, for producing an acyl derivative of tylosin and the acid addition salts thereof wherein the acylation of the hydroxyl group at the 3-position of the derivative of tylosin in which $R_2'$ at the 4″-position is n-butyryl group, as shown in formula I′ is propionylation.

8. A process, as claimed in claim 2, for producing an acyl derivative of tylosin and the acid addition salts thereof wherein the acylation of the hydroxyl group at the 3-position of the derivative of tylosin in which $R_2'$ at the 4″-position is isovaleryl group, as shown in formula I′ is propionylation.

9. A process, as claimed in claim 1, for producing acyl derivatives of tylosin and the acid addition salts thereof wherein the hydroxyl group at the 4″-position of tylosin or the hydroxyl group at the 4″-position of the derivative of tylosin in which $R_1'$ at the 3-position is hydrogen or acyl group, as shown in formula I′ is acylated.

10. A process, as claimed in claim 9, for producing an acyl derivative of tylosin and the acid addition salts thereof wherein the acylation of the hydroxyl group at the 4″-position of tylosin, as shown in formula I′, is n-butyrylation.

11. A process, as claimed in claim 9, for producing an acyl derivative of tylosin and the acid addition salts thereof wherein the acylation of the hydroxyl group at the 4″-position of tylosin, as shown in formula I′, is isovalerylation.

12. A process, as claimed in claim 9, for producing an acyl derivative of tylosin and the acid addition salts thereof wherein the acylation of the hydroxyl group at the 4″-position of the derivative of tylosin in which $R_1'$ at the 3-position is acetyl group, as shown in formula I′ is n-butyrylation.

13. A process, as claimed in claim 9, for producing an acyl derivative of tylosin and the acid addition salts thereof wherein the acylation of the hydroxyl group at the 4″-position of the derivative of tylosin in which $R_1'$ at the 3-position is acetyl group, as shown in formula I′ is isovalerylation.

14. A process, as claimed in claim 9, for producing an acyl derivative of tylosin and the acid addition salts thereof wherein the acylation of the hydroxyl group at the 4″-position of the derivative of tylosin in which $R_1'$ at the 3-position is propionyl group, as shown in formula I′ is n-butyrylation.

15. A process, as claimed in claim 9, for producing an acyl derivative of tylosin and the acid addition salts thereof wherein the acylation of the hydroxyl group at the 4″-position of the derivative of tylosin in which $R_1'$ at the 3-position is propionyl group, as shown in formula I′ is isovalerylation.

16. A process, as claimed in claim 1, for producing acyl derivatives of tylosin and the acid addition salts thereof wherein the hydroxyl group at the 3- and 4″-positions of tylosin, as shown in formula I′, are each acylated with different acyl groups.

17. A process, as claimed in claim 16, for producing an acyl derivative of tylosin and the acid addition salts thereof wherein the acylation of the hydroxyl group at the 3-position of tylosin, shown in formula I′, is acetylation and the acylation of the hydroxyl group at the 4″-position of the same is n-butyrylation.

18. A process, as claimed in claim 16, for producing an acyl derivative of tylosin and the acid addition salts thereof wherein the acylation of the hydroxyl group at the 3-position of tylosin, shown in formula I′, is acetylation and the acylation of the hydroxyl group at the 4″-position of the same is isovalerylation.

19. A process, as claimed in claim 16, for producing an acyl derivative of tylosin and the acid addition salts thereof wherein the acylation of the hydroxyl group at the 3-position of tylosin, shown in formula I′, is propionylation and the acylation of the hydroxyl group at the 4″-position of the same is n-butyrylation.

20. A process, as claimed in claim 16, for producing an acyl derivative of tylosin and the acid addition salts thereof wherein the acylation of the hydroxyl group at the 3-position of tylosin, shown in formula I', is propionylation and the acylation of the hydroxyl group at the 4''-position of the same is isovalerylation.

21. A process, as claimed in claim 1, for producing acyl derivatives of tylosin and the acid addition salts thereof wherein a microorganism belonging to the genus Streptomyces and capable of acylating at least one of the hydroxyl groups at the 3- and 4''-positions of tylosin or the derivatives of tylosin, shown in the formula I', which is selected from the group consisting of *Streptomyces thermotolerans* ATCC 11416, *Streptomyces fungicidicus* subsp. *espinomyceticus* ATCC 21574, *Streptomyces mycarofaciens* ATCC 21454 and *Streptomyces hygroscopicus* ATCC 21582 is used in the presence of $C_2$–$C_5$ acyl donor.

22. A process, as claimed in claim 1, for producing acyl derivatives of tylosin and the acid addition salts thereof wherein acylation is carried out in the cultivated broth of a microorganism belonging to the genus Streptomyces and capable of acylating at least one of the hydroxyl group at the 3- and 4''-positions of tylosin or the derivatives of tylosin, as shown in the formula I', in the presence of at least one acyl donor selected from the group consisting of acetyl CoA, propionyl CoA, n-butyryl CoA, isovaleryl CoA and the precursors of acyl CoAs.

23. A process, as claimed in claim 22, for producing acyl derivatives of tylosin and the acid addition salts thereof wherein a quantity of the carbon source and the nitrogen source in the medium and a sort of substrate are adjusted depending on the acyl groups used for the acylation of hydroxyl groups at the 3- and 4''-positions of tylosin or derivatives of tylosin as shown in formula I'.

24. A process, as claimed in claim 1, for producing acyl derivatives of tylosin and the acid addition salts thereof wherein a microorganism is used in the form of a cell suspension in a liquid medium selected from the group consisting of water, buffer solution and broth filtrate, in the presence of at least one acyl donor selected from the group consisting of acetyl CoA, propionyl CoA, n-butyryl CoA, isovaleryl CoA and precursors of acyl CoAs, said suspension being prepared by cultivating a microorganism belonging to the genus Streptomyces which is capable of acylating at least one hydroxyl group at the 3- and 4''-positions of tylosin or the derivatives of tylosin, as shown in formula I', collecting the cells thus produced and suspending them in said liquid medium.

25. A process, as claimed in claim 1, for producing acyl derivatives of tylosin and the acid addition salts thereof wherein the acylation is enzymatically carried out in the presence of an enzyme preparation of a microorganism belonging to the genus Streptomyces and capable of acylating at least one hydroxyl group at the 3- and 4''-positions of tylosin or derivatives of tylosin shown in formula I' and in the presence of at least one acyl donor selected from the group consisting of acetyl CoA, propionyl CoA, n-butyryl CoA and isovaleryl CoA.

* * * * *

UNITED STATES PATENT AND TRADEMARK OFFICE
CERTIFICATE OF CORRECTION

PATENT NO. : 4,201,843
DATED : May 6, 1980
INVENTOR(S) : Rokuro Okamoto, et al

It is certified that error appears in the above—identified patent and that said Letters Patent is hereby corrected as shown below:

Attached Sheet 24 of the drawings containing Fig. 24 should be inserted as part of the above-identified patent.

Signed and Sealed this

Eleventh Day of November 1980

[SEAL]

Attest:

SIDNEY A. DIAMOND

Attesting Officer

Commissioner of Patents and Trademark